United States Patent [19]

Tate, Jr.

[11] 4,105,302
[45] Aug. 8, 1978

[54] AUTOMATIC REFRACTION APPARATUS AND METHOD

[76] Inventor: George W. Tate, Jr., 11127 Bushire, Dallas, Tex. 75229

[21] Appl. No.: 699,076

[22] Filed: Jun. 23, 1976

[51] Int. Cl.² .......................... A61B 3/14; A61B 3/10; A61B 3/00
[52] U.S. Cl. .......................................... 351/7; 351/6; 351/13; 351/30; 351/39
[58] Field of Search ...................... 351/6, 17, 30, 7, 13, 351/34, 28, 36, 24, 39

[56] References Cited
U.S. PATENT DOCUMENTS

| 2,464,547 | 3/1949 | Allyn | 351/6 |
| 3,490,832 | 1/1970 | Mitsuishi | 351/36 |
| 3,524,702 | 8/1970 | Bellows et al. | 351/13 |
| 3,624,497 | 11/1971 | Max et al. | 351/7 |
| 3,969,020 | 7/1976 | Lynn et al. | 351/28 |

Primary Examiner—Paul A. Sacher
Assistant Examiner—Rodney Bovernick

[57] ABSTRACT

Apparatus and method provide for automatically measuring the refractive error of a subject's eye and thus the prescription for lens or eye glasses for correcting this error. Under the control of a programmed automatic data processing system, an objective refraction measurement is made. Test symbols are then alternately presented to the subject under control of the data processing system. The symbols are viewed by the subject through an optical system whose refractive power may be continuously varied under control of the data processing system. The initial setting of the optical system is based upon the objective refraction measurement. The data processing system varies the size of the symbols presented to compensate for the power of the optical system so that a given symbol will appear to the subject to be of constant size. In one illustrative embodiment of the present invention, the subject communicates with the data processing equipment via a subject response device to indicate his preference for one or the other of the presented symbols. The data processing system interprets the responses to modify the setting of the optical system, alter the presentation of symbols and elicit another response from the subject. The subjective refraction is continuously monitored by objective refraction to ensure optimization of the refractive correction.

12 Claims, 22 Drawing Figures

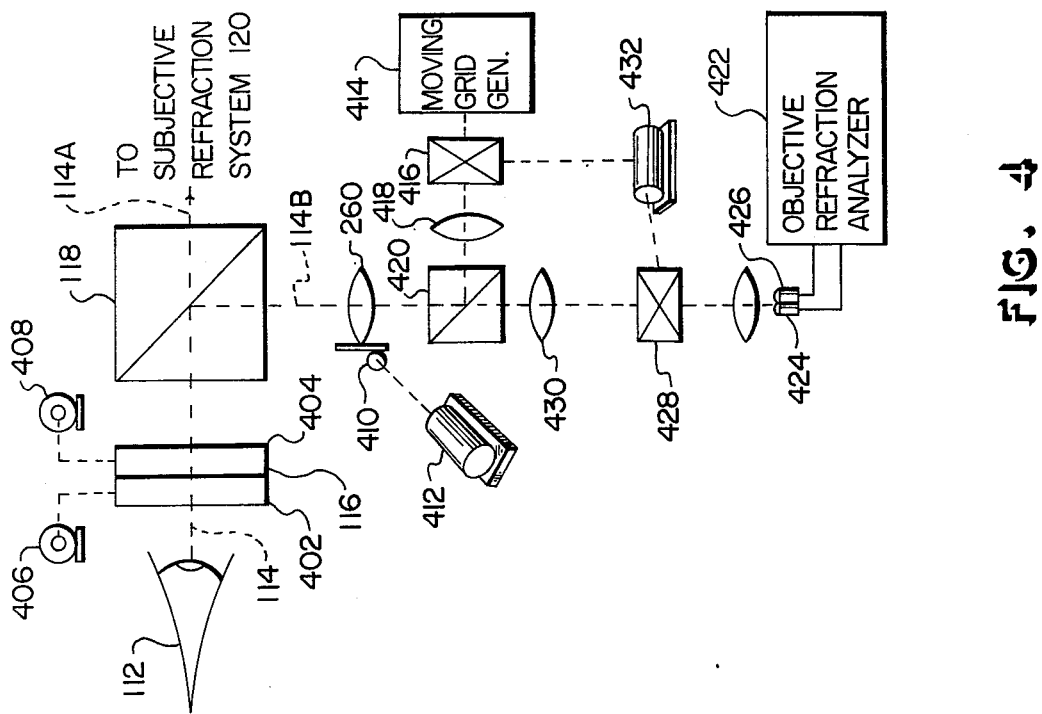
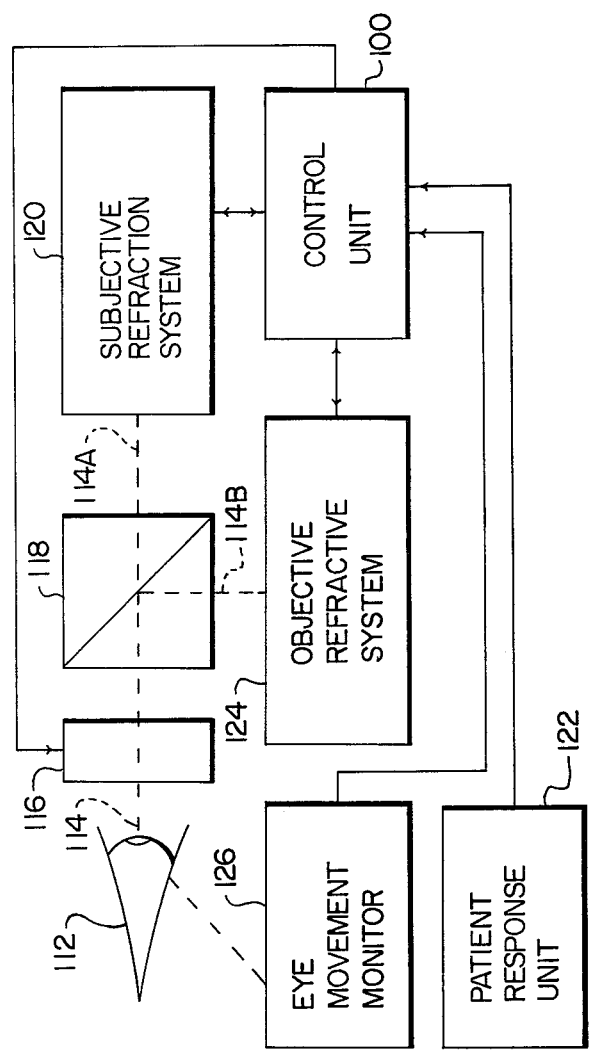
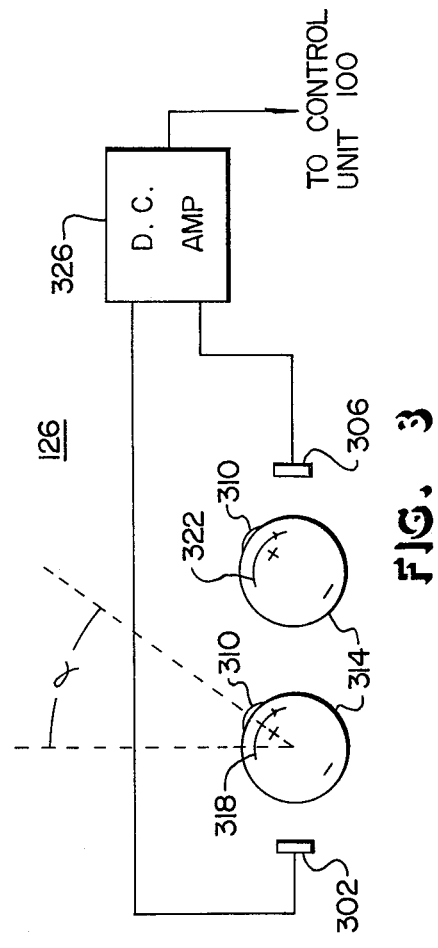
FIG. 4
FIG. 1
FIG. 3

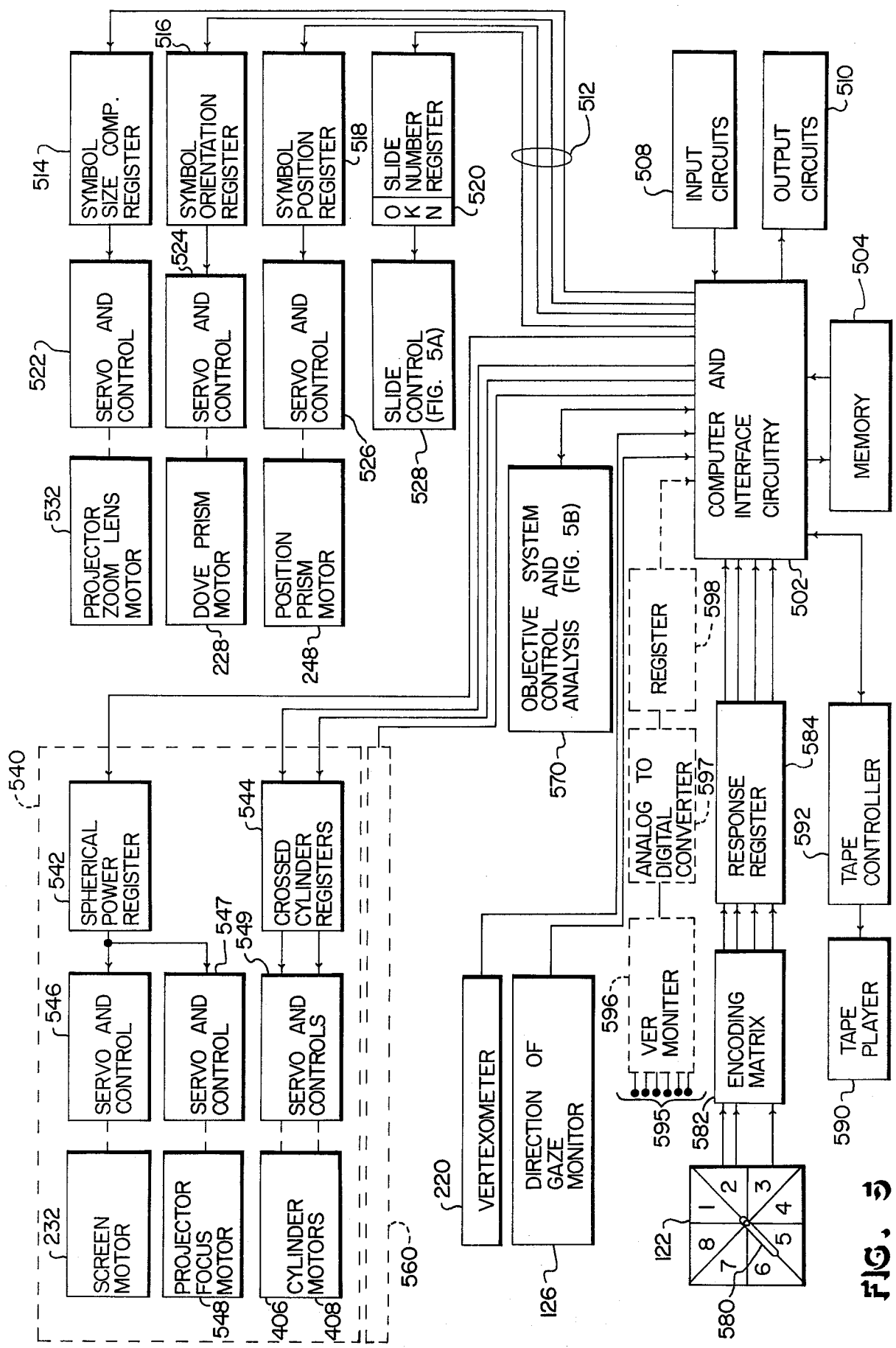

STAGE C, D, G, AND J TESTS

|    | C    | D   | G   | J   |
|----|------|-----|-----|-----|
| $N_1$ | 4    | 4   | 8   | 10  |
| $N_2$ | 2    | 2   | 4   | 5   |
| $N_3$ | 2    | 2   | 4   | 8   |
| A  | 90°  | 45° | 45° | 90° |
| B  | 0.25 | 0.5 | 1   | 2   |

AUTOMATIC REFRACTION APPARATUS AND METHOD

BACKGROUND OF THE INVENTION

This invention relates to the field of human eye examination and more particularly to apparatus and method for automatically measuring refractive error in the vision of a human patient.

Light entering a human eye is refracted (bent) by the cornea and lens of the eye to converge and focus to some location behind the lens. If light from a distant object (theoretically at infinity) focuses on the retina of the eye then, if there is no distortion due to astigmatism (discussed momentarily), the eye is considered free from refractive error. When this is the case, the person can see distant objects clearly. In order to view a new object clearly, i.e., cause light from the object to converge and focus on the retina, it is necessary that the curvature of the lens of the eye be increased. This is achieved by the action of a muscle and is called "accommodation".

If light from a distant object converges to a point in front of the retina, the distant object is not seen clearly by the person and the person is said to be nearsighted. This "refractive error" of the eye can be corrected by an eye glass or lens which causes light from distant objects to diverge slightly as it passes through the lens. Such a lens is considered to have "negative refractive power". The light then passes through the lens of the eye and focuses on the retina thus enabling the person to clearly see the distant object.

If light from a distant object passes through the lens of the eye and converges toward a point behind the retina of the eye, then the person is said to be farsighted. Such a person may "accommodate" to place distant objects in focus, but near objects will not be seen sharply without additional accommodation. The farsighted condition may be corrected by placing an eyeglass or lens having "positive refractive power" between the eye and the object with such lens causing light from distant objects to converge as the light passes through the lens. The light then passes through the lens of the eye to focus on the retina so that distant objects can be viewed effectively, without accommodation. Near objects, of course, will still require accommodation.

Astigmatism was referred to earlier as causing a distortion of the focusing of light passing through the lens of the eye. Astigmatism is a condition in which the first refracting surface of the eye, i.e., the cornea, has unequal curvature which prevents the focusing of light to a common point on the retina. Correction of this condition is accomplished by means of an eyeglass or lens having cylindrical curvature. Cylindrical curvature is that curvature represented by the side of a cylinder (as opposed to spherical curvature which is that represented by the surface of a sphere). Cylindrical and spherical lenses may be either positive or negative, with positive lenses being ones which are thicker in the middle than at the edge and negative lenses being ones which are thinner in the middle than at the edge. Positive and negative refractive lenses were mentioned above when describing correction of refractive errors in the eye. By orienting a negative or minus cylindrical lens of appropriate power so that its long axis (the axis perpendicular to the direction of maximum curvature) is overlying and parallel with the positive astigmatic axis of the eye (the axis perpendicular to the direction of greatest curvature of the front surface of the eye), astigmatism may be corrected. The effect of such a cylindrical lens is to perform refraction of light in a direction perpendicular to the axis of astigmatism and by an amount sufficient to compensate for the difference in curvature of the surface of the eye.

Lens power is the ability of a lens to refract light, i.e., to converge light if the lens is positive or to diverge light if the lens is negative. Lens power is measured in diopters, which is the reciprocal of the focal length of the lens, measured in meters. The focal length of a lens is defined as the distance from the lens to a point (for spherical lens) or line (for cylindrical lens) at which light converges after the light enters the lens in parallel and passes therethrough (for a positive lens) or from which the light appears to diverge after entering the lens and passing therethrough (for a negative lens). These definitions are well-known in the field of optics and ophthalmology.

At the present time, eye examinations to determine the prescription of eyeglasses to correct nearsightedness, farsightedness and astigmatism are performed manually by ophthalmologists, optometrists, and technician refractionists. These examinations generally begin with some type of rough screening to determine generally if the eye is nearsighted or farsighted. A number of objective measurements may be utilized for this rough screening including retinoscopy. In retinoscopy, the Examiner makes a rough determination of the refractive error of the subject's eye by positioning a so-called trial lens (one or a number of lenses having different corrective powers used for eye examinations), introducing a slit of light into the subject's eye, moving the slit of light at right angles to the length of the slit, and observing how it is reflected from the retina of the eye. The Examiner is able to determine generally the refractive error of the eye by the way the reflected light moves as the slit of light is moved and by changing the power of the trial lens until certain conditions of reflected movement are met.

Another kind of rough screening may be performed by alternately placing medium power plus and minus spherical lenses before the eye, superimposed with a trial lens, as the subject views a displayed object or symbol. The subject's indication of which medium power spherical lens provides the sharper viewing of the symbol guides the Examiner in changing the trial lens to solicit another choice from the subject. For example, if a plus power trial lens is being used and the subject indicates a preference for the combination of the trial lens and the plus spherical lens, then the Examiner changes the trial lens to be slightly more positive and again queries the subject as to which combination of the trail lens and the plus and minus spherical lens is preferred. An approximation of the power necessary to correct the subject's refractive error is indicated by a reversal in the subject's choice of the plus spherical lens combination over the minus spherical lens combination as he compares the two. It will be recognized that in this type of rough screening, the subject is usually choosing between two rather blurred images. For this reason, only a rough approximation of the correct power can be made.

If the previous eyeglass prescription is available either in written form or from the eyeglasses themselves, this information may be used in place of performing the rough screening. This is especially true if the subject can see fairly well with such eyeglasses since then, only a small adjustment may be necessary to correct the refractive error.

A final, more sophisticated form of "Rough Screening" is currently available in the form of Automatic Objective Refractors which in essence perform the equivalent of retinoscopy very rapidly and accurately. Although they are usually more accurate than a human retinoscopist, eyeglasses may not be prescribed from their output if the patient is to be maximally comfortable in his spectacles.

Further refinement of the rough screening results is necessary if the subject is to see clearly. This refinement may be either so-called "subjective refinement" requiring a conscious response by the subject as to his preference of, for example, displayed symbols, or objective refinement in which no conscious response is required of the subject. In either type of test, the purpose is to determine which corrective lenses will maximize the subject's visual acuity, that is, his ability to discriminate and identify the shapes of symbols of certain sizes displayed at a certain distance from the subject. Visual acuity is usually designated by fractions such as 20/20, 20/30, etc., in which the numerator represents the distance between the subject and the displayed symbols and the denominator represents a measure of the size of a symbol barely discernable by the subject. This size is in terms of the distance which a normal subject could see the symbol. For example, 20/40 means that the subject could barely read a symbol at 20 feet which a person with normal vision (20/20) could read at 40 feet.

An alternative way of expressing this same information would be to represent this fraction as its decimal equivalent. Thus, 20/20 = 1, 20/40 = 0.5 and so on. Distances may also be expressed in meters (20/20 = 6/6, where 6 meters = 19.7 feet). These latter expressions are most common outside the United States.

One type of objective refinement involves the measurement of the occipital-lead electroencephalograms of a subject as he views test symbols with different trial lens configurations. These "visually evoked responses" (VER) may then be examined to determine the visual acuity of the subject as a function of the amplitudes of the signals recorded on the electroencephalograms. When the visual acuity is a maximum, the signal amplitude will be maximum.

Another type of objective examination for testing visual acuity is known as optokinetic nystagmus (OKN). In this test, the reflex "following movement" of the eye is monitored as black and white vertical bars are moved horizontally across a screen in front of an eye. The eye of a subject with good visual acuity will, by reflex action, fix upon one of the bars, follow it until it becomes difficult or impossible to see, and then jerk quickly back to assume fixation on another bar, with the following rate of the eye matching the rate of bar movement. The visual acuity is inversely proportional to the width of the bars required for the "following movement" to be elicited. Thus, a subject with poor vision requires larger bars than does a patient with good vision to exhibit the appropriate "following movement" of the eye.

Even if an accurate final prescription for eyeglasses can be determined by one of the objective refinement tests, the subject may be so accustomed to accommodating in order to see clearly that eyeglasses which eliminate the need for such accommodation are undesirable to the subject. Subjective refinement enables the Examiner to determine an eyeglass prescription which will provide the subject with maximum comfort. This may be desirable even if some sacrifice in sharpness of the visual image must be suffered. Thus, subjective refinement is generally desirable and this type of testing is the most difficult and time-consuming part of an eye examination. Much patience is required on the part of the Examiner and persistent attention to detail on the part of the subject. If the subject feels rushed or gets bored, a hasty and incorrect decision may lead the Examiner in the wrong direction in presenting test lenses to the subject. Back-tracking may thus be required, but even if it isn't, rechecking is often desirable to ensure the accuracy of the examination.

It is an object of the present invention, in view of the above-described methods for manually measuring refractive error, to provide an automatic refraction apparatus and method implemented by automatic data processing equipment in combinaton with test symbol projection apparatus and a trial lens system.

It is another object of the present invention to provide an automatic apparatus and method for subjectively determining the refractive error of a subject rapidly and accurately.

Presently-used trial lens systems consist of a pair of rotatable turrets, each holding lenses of different power about the periphery thereof. The different trial lenses in one turret may be rotated into position in front of one of the subject's eye while the lenses in the other turret may be rotated into position in front of the other eye of the subject. The subject views test symbols through the lenses in the turrets and expresses, for each eye, a preference for one lens of each of successively presented pairs of lenses. This is usually done by simply rotating one lens of a pair in front of an eye then rotating the other lens of the pair in front of the eye and asking the subject to express his preference. As is evident from the above description, the power of the lenses positioned in front of the eye is varied by discrete "jumps" with manual rotation of the turret. Thus, the accuracy of the determination of the refractive error is dependent, in part, on the magnitude of the lens power increments which can be presented to the subject.

It might be noted here that some turrets include two or even three coaxial, contiguous elements, each of which holds a plurality of lenses of different power. Each element is independently rotatable so that each lens of each element may be effectively aligned with each lens of the other elements. In this manner, the many different combinations of lenses provide a fairly large number of different trial lens powers which may be presented to the subject; however, the trial lens power changes must still be made in discrete jumps.

Another problem with the currently used turret systems is that the number of lenses through which the subject is to view the test symbol can vary depending upon the positioning of the turret elements. For example, for one setting three lenses may be positioned before the subject whereas for another setting, only one or two lenses may be aligned because one of the turret elements is positioned so that only an opening (with no lens) in the element is aligned with the other lens or lenses. Of course, with variations of the number of lenses through which a test symbol is viewed, light transmission through the lens combinations varies and thus the relative brightness of the symbol varies. This may adversely influence the preferences expressed by the subject in choosing between the test symbols.

it is still another object of the present invention to provide automatic refraction apparatus and method having an optional system of continuously variable power through which the subject views a test symbol.

It is also an object of the present invention to provide apparatus and method for automatically controlling the variation in power of the optical system.

It is a further object of the present invention to provide such an optical system in which the number of lenses before an eye is maintained constant as the power of the optical system is varied.

If a test symbol of fixed size is presented on a screen for viewing by a subject, and the power of the lens system is varied, it will appear to the subject that the size of the symbol varies. Thus, when the subject is called upon to indicate a preference based on sharpness or clearness, between the test symbol viewed through the lens system of one power and the test symbol viewed through the lens system of a different power, the subject may be influenced by the size of the symbol. This is undesirable and even though the subject is cautioned against this, his preferences may still be influenced by the size of the symbol.

It is therefore an object of one aspect of the present invention to provide refraction apparatus and method for automatically varying the size of a test symbol for given visual acuity presented for viewing by a subject to compensate for changes in power of the optical system through which the subject is viewing the symbol.

It is also an object of this aspect of the present invention to automatically control the magnification of test symbols so that they appear to be of constant size to a subject regardless of the variation in power of the optical system through which the subject is viewing the symbol.

As discussed above, in the course of an eye examination to determine refractive error using presently known techniques, a subject is called upon to indicate a preference between a test symbol viewed through one set of trial lens (Hereafter called "Prescription") and the same test symbol viewed through a different set of trial lens (or prescription). Preferences are solicited for successive pairs of lens combinations compared with the test symbol being presented at the same location on a screen. The examiner successively presents the trial lens of each pair to the subject and the subject then indicates a preference either for the "previous" Prescription of the "present" Prescription (or something similar to this). Because the subject must indicate a preference between what appears to be consecutively presented symbols at the same location on the test screen, confusion can arise in the course of the subject attempting to communicate his preferences to the examiner.

It is an object of another aspect of the present invention to provide apparatus and method for presenting test Prescriptions alternately for viewing by a subject to thereby enable the subject to indicate a preference by identifying the "preferred" Prescriptions.

It is also an object of the present invention to provide a manual response device by which a subject can identify which of two presented test symbols is the "preferred" test symbol.

When asked to express a preference between two presented Prescriptions, patients have a tendency to become "locked-in" on choosing, for example, the second presented Prescription over the first. Oftentimes, a person will keep on choosing the second Prescription until he is well past the point of optimal visual acuity and with each succeeding selection, the patient's visual acuity will actually decrease. Therefore, frequent measurements of visual acuity should be taken to ensure that the optimal visual acuity is achieved. Alternatively, an objective refraction measurement may be periodically taken, or the retinal image quality periodically measured. Finally, the magnitude of the difference between the two Prescriptions may be optimized to make the choice for the subject as easy and as obvious as possible, considering his visual acuity. If these latter measurements are done by presently known manual means after each subjective measurement, this would prove to be extremely time consuming.

It is an object of another aspect of the present invention to provide apparatus for automatically objectively refracting the subject's eye periodically during the process of the subjective testing.

It is still another object of the present invention to inform the patient when a subjective response results in decreased retinal image quality.

It is yet another object of the present invention to change the magnitude of the difference between two choices of Prescription in an optimum fashion as a function of visual acuity.

Diseases of the eye take on different forms. Some diseases interfere with transmission of light to the retina. For example, corneal disease or cataracts present blurred images to the retina. Retinal and neural problems, such as for example macular degenerations or neurological diseases (e.g. Multiple Sclerosis, tumors, etc.) also interfere with overall visual acuity. If a good visual acuity cannot be obtained and the retinal image quality is good, this indicates possible retinal and neural problems. If a good visual acuity cannot be obtained and the retinal image quality is poor, this indicates the possibility of cataracts or other refractive media problems.

It is therefore an object of this aspect of the present invention to provide apparatus which gives a measure of optical quality in correlation with final visual acuity to detect the possibility of disease and give a differential diagnosis thereof.

SUMMARY OF THE INVENTION

The above and other objects and advantages of the present invention are realized in apparatus and method for determining the refractive error of a subject under control of a programmable automatic data processing system. An objective refraction measurement is first made. Then test symbols are presented alternately to the subject. The subject views the test symbols through a continuously variable optical system controlled by the automatic data processing equipment. The optical system is controlled to provide one power setting for the first symbol presented and a different power setting (Prescription) for the second symbol presented. The subject indicates a preference for the first or second presented symbol (and thus Prescription) based on sharpness and visual clarity of the symbol by operating a manual response device identifying the choice. The subject's response is then used by the data processing equipment to automatically control the power settings of the optical systems for subsequently presented test symbols. Periodic, and preferable frequent, objective and/or subjective visual acuity tests are made and the objective test results used by the data processing equipment in conjunction with the patient responses to control the power settings of the optical system. Additionally, objective refraction measurements are periodically made as a check against the patient's subjective responses.

In accordance with one aspect of the invention, the size of the test symbols is controlled by the data processing equipment in conjunction with the control of the power setting of the optical system so that the two test symbols will appear to the subject to be the same size regardless of the variation in power of the optical system.

BRIEF DESCRIPTION OF THE DRAWINGS

The present invention, both as to its organization and manner of operation, together with further objects and advantages thereof may be best understood by way of illustration and example, when taken in conjunction with the accompanying drawing, in which:

FIG. 1 is an overall block diagram of an illustrative system according to the present invention;

FIG. 3 is a diagrammatic showing of an electrooculograph monitor;

FIG. 4 is a block diagram of an objective refraction system which illustratively is utilized in the system of FIG. 1;

FIG. 5, 5A and 5B, when taken together, form a block diagram of one system embodiment of the present invention;

Figure 8A:
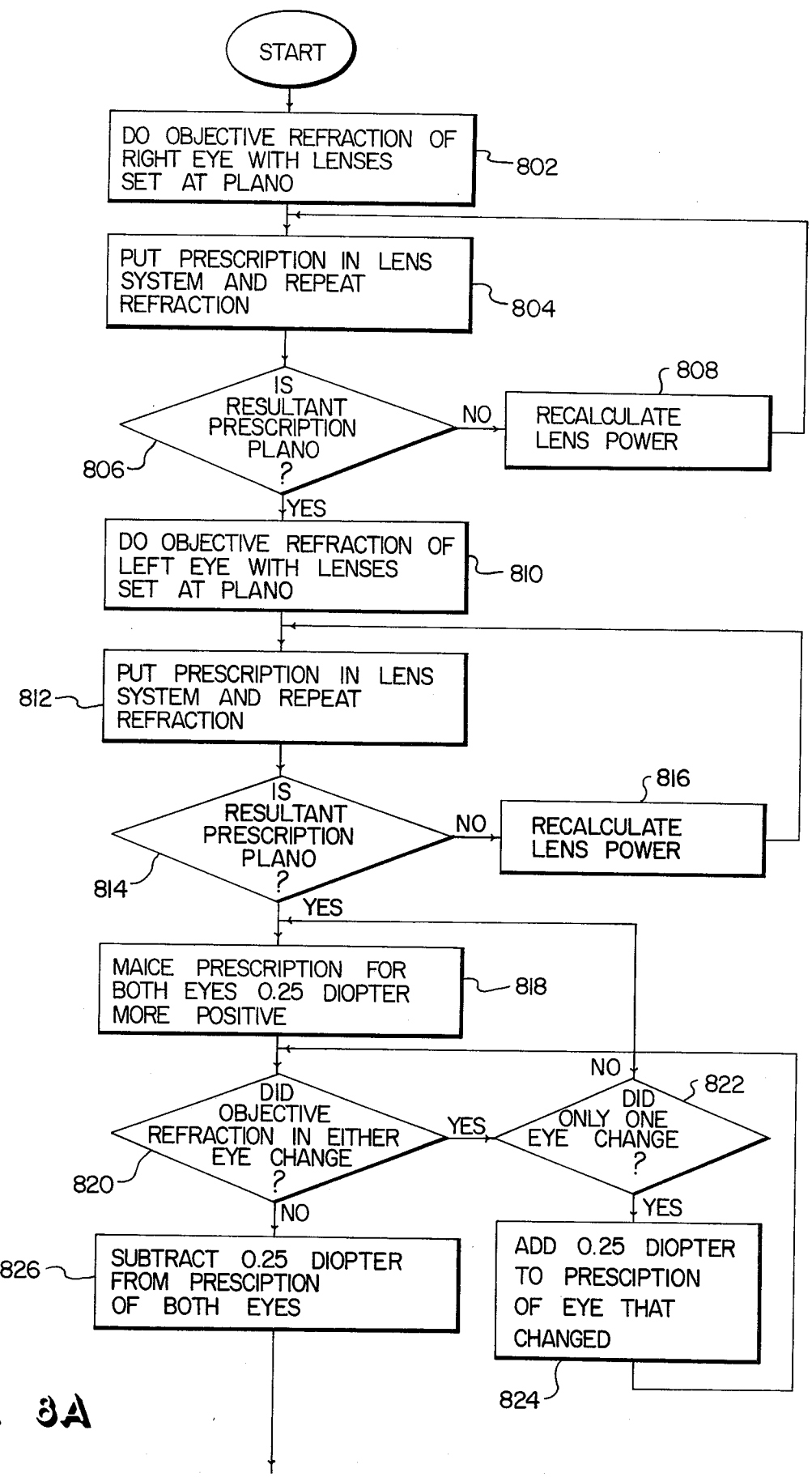
Figure 8B:
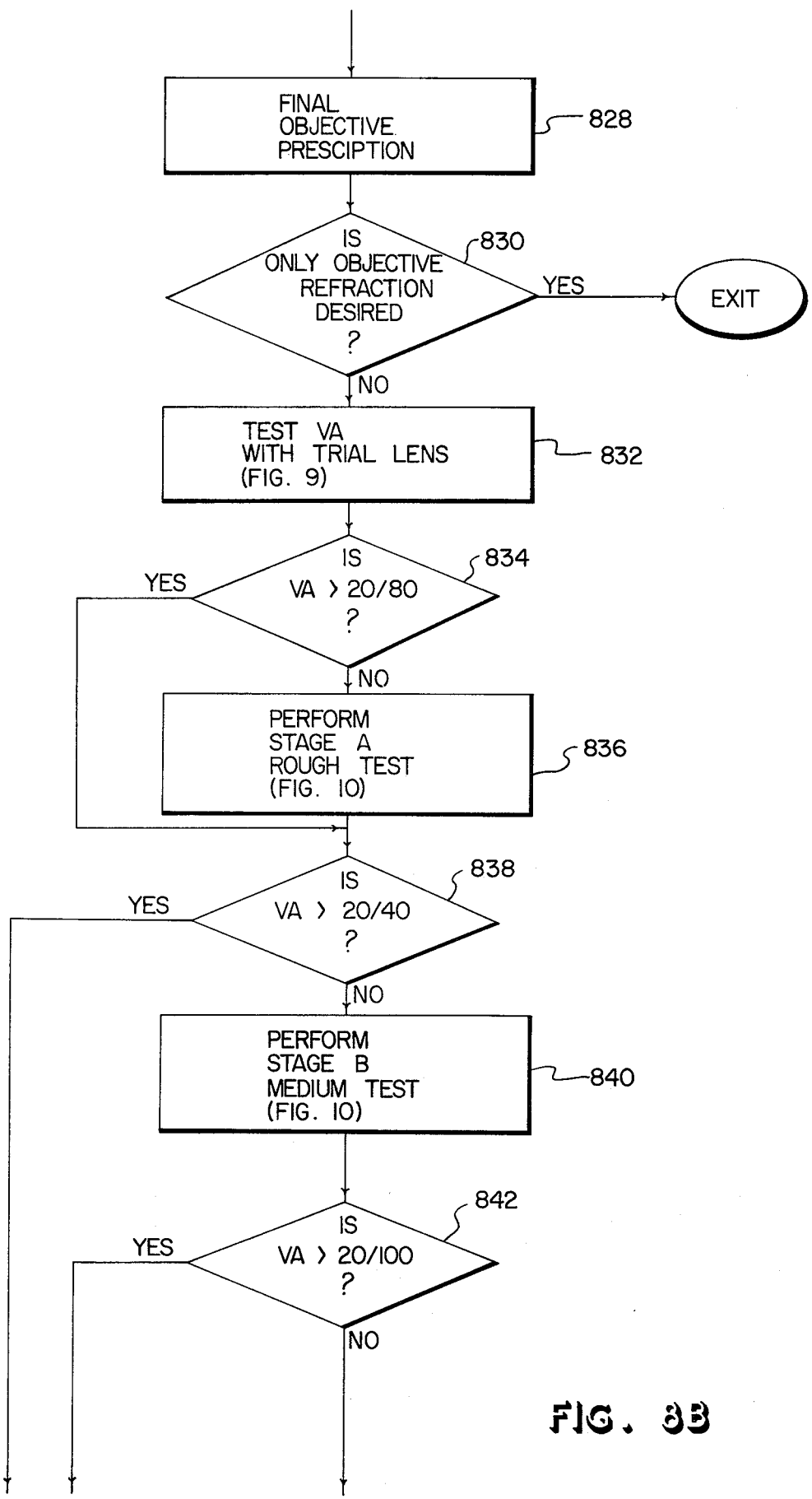
Figure 8C:
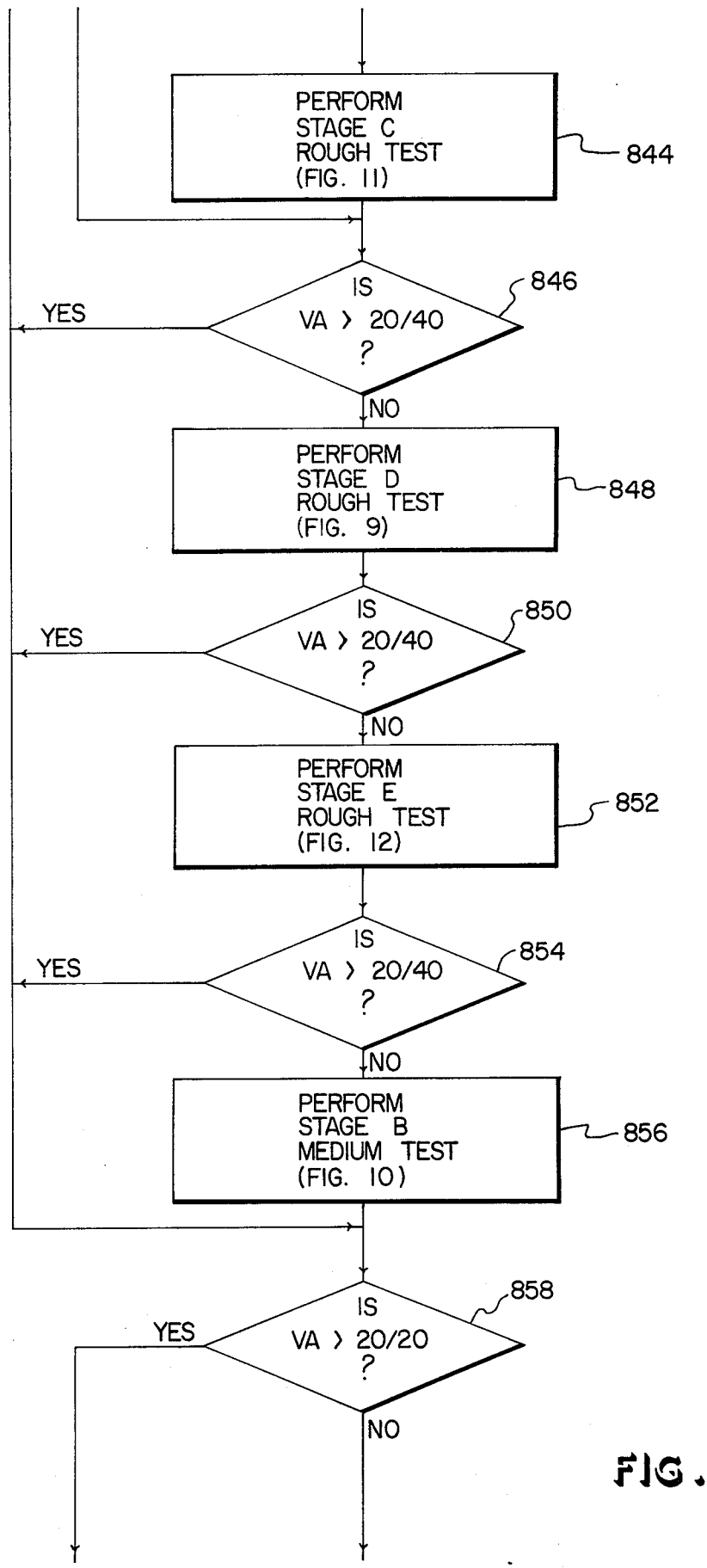
Figure 8D:
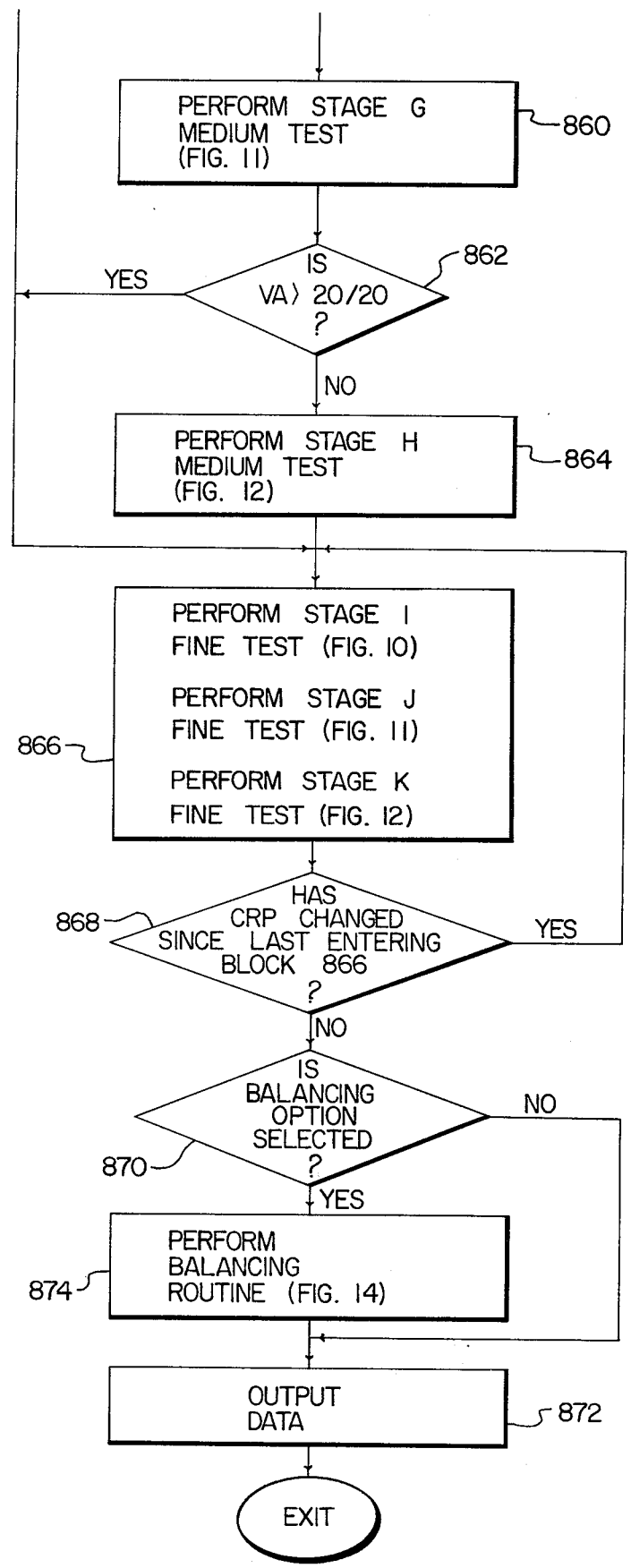
Figure 9A:
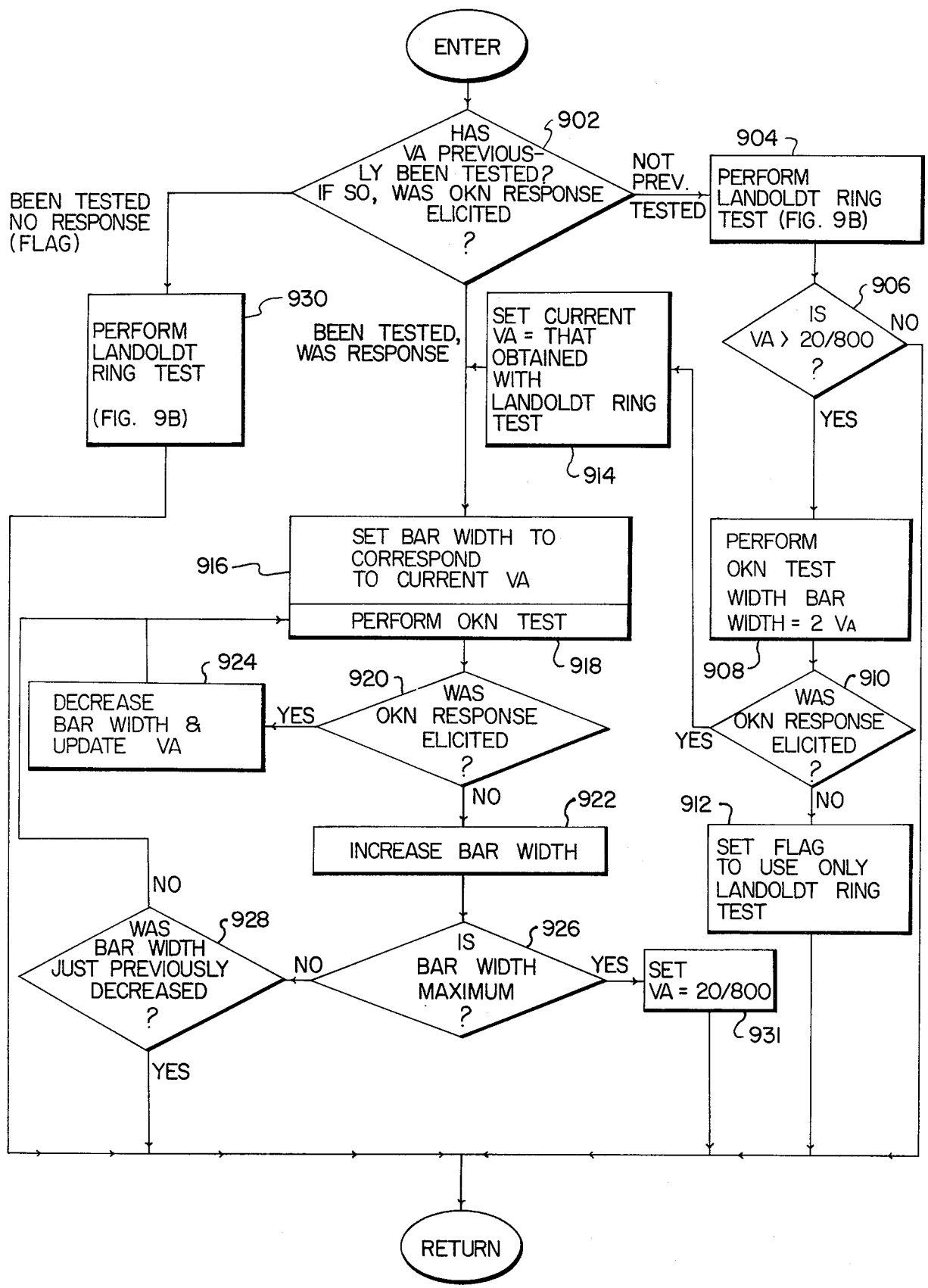
Figure 9B:
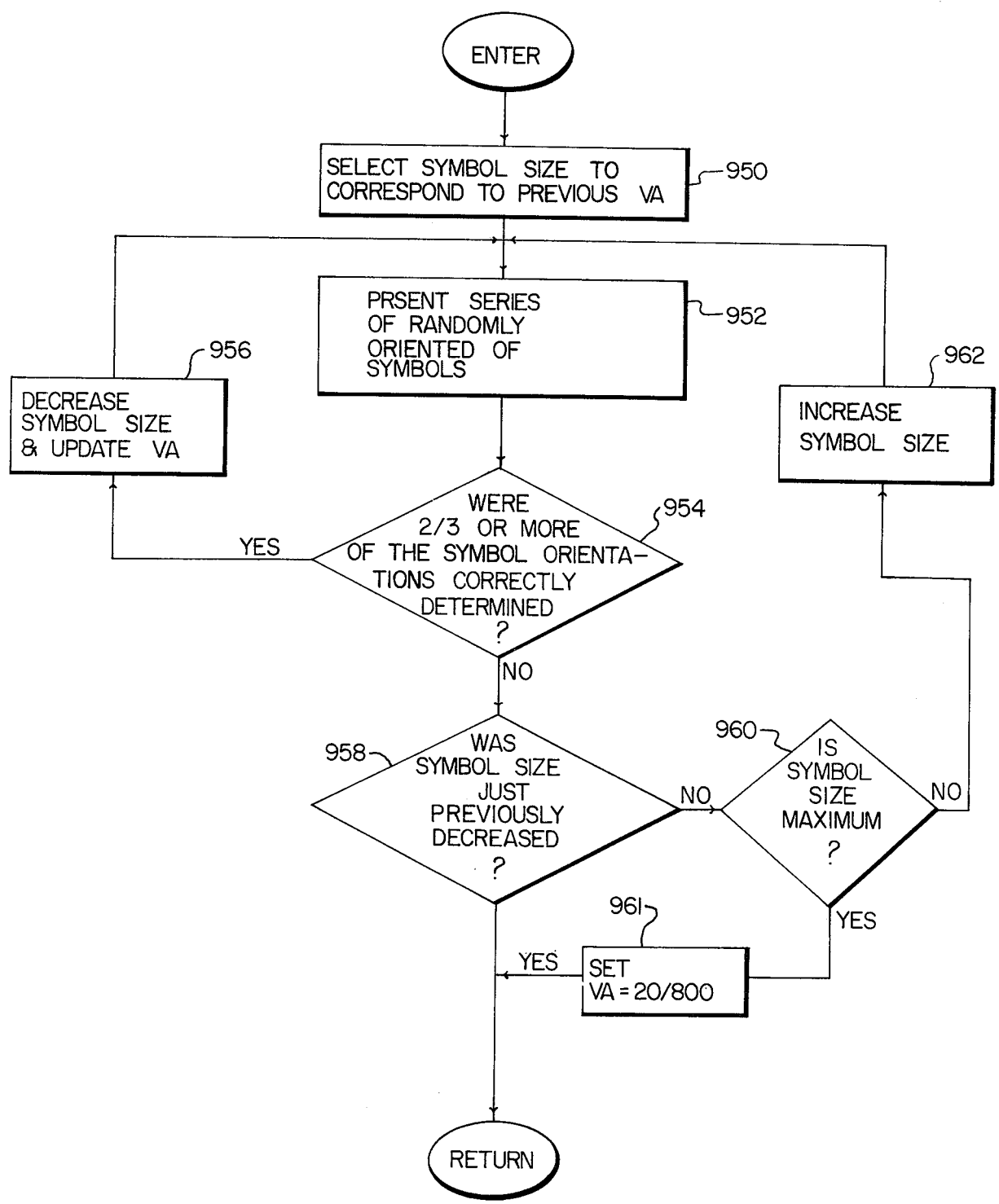

FIS. 8A, 8B, 8C and 8D are a flow chart of one illustrative process or program for utilizing the apparatus for FIGS. 1, 2, 5, 5A and 5B to perform refractive error tests;

FIGS. 9A and 9B are flow charts of a subprogram of the FIG. 8 program for testing visual acuity; and FIGS. 10, 11A, 11B, 12A, 12B, 13 and 14 are flow charts of subprograms of the program of FIG. 8.

DESCRIPTION OF THE PREFERRED EMBODIMENT

Referring now to FIG. 1, shown therein is an overall block diagram depicting the interaction of the various major subsystems of a system constructed in accordance with the principles of this invention. The operation of the system is entirely under the control of control unit 100 which is preferably a programmed automatic data processor or computer. Each of the different subsystems feeds information to control unit 100 and is controlled by control unit 100 at each step of the examination in accordance with the information received by control unit 100. The subject being examined is placed in such a position that its eye 112 sights along an optical path 114 which first passes through variable crossed cylinder 116. The power and axis of variable crossed cylinder 116 is controlled by a servo (not shown) which operates in response to signals received from control unit 100. Optical path 114 next passes through beam splitter 118 which breaks up path 114 into paths 114A and 114B. Path 114A is directed to subjective refraction system 120 which operates in response to signals received from control unit 100 to present test symbols to the subject and elicit a response therefrom. The subject responds via patient response unit 122, coupled to control unit 100. Throughout the entire time the subject is being subjectively refracted, control unit 100 is also making objective refraction measurements by means of objective refraction system 124 which is in line with optical path 114B. Among the purposes of objective refraction system 124, is the insurance that the subjective responses are reasonable. Basically, the objective refraction system 124 monitors the subjective refraction system 120.

At the start of the examination process, an objective refraction is done. Then a subjective refraction is done. At each step, however, the objective refraction system 124 measures the retinal image quality. A visual acuity test must be made only when the retinal image quality falls or when the program logic requires this information. If the visual acuity is the same or better than before, the subjective response is again taken. If the visual acuity is worse, the system is reset to where the retinal image quality and visual acuity are at a maximum. A message is given the patient, and the test is resumed. If it appears that subjective responses from the subject bear no relation to the test so that the subject cannot be refracted subjectively, then an objective prescription or the best subjective prescription is obtained, whichever produces the best acuity. It should be noted that some patients (e.g. small children) are not candidates for subjective refraction, and in this event the operator has the option of performing only an objective refraction. In the event a good visual acuity of the subject cannot be obtained, then the retinal image quality is examined. A high retinal image quality under such circumstances would indicate the possibility of retinal or neural problems. If there is a low retinal image quality, this would indicate cataracts or other refractive media problems.

An eye movement monitor unit 126 may be optionally included in the system if the tests utilizing the subjective refraction system 120 require the subject to examine symbols at different locations. Since both eyes are being tested, variable cross cylinder 116, beam splitter 118, subjective refraction system 120 and objective refraction system 124 must be duplicated for each eye. This may be accomplished for the objective system by "time sharing" a single system between the two eyes.

Figure 2:
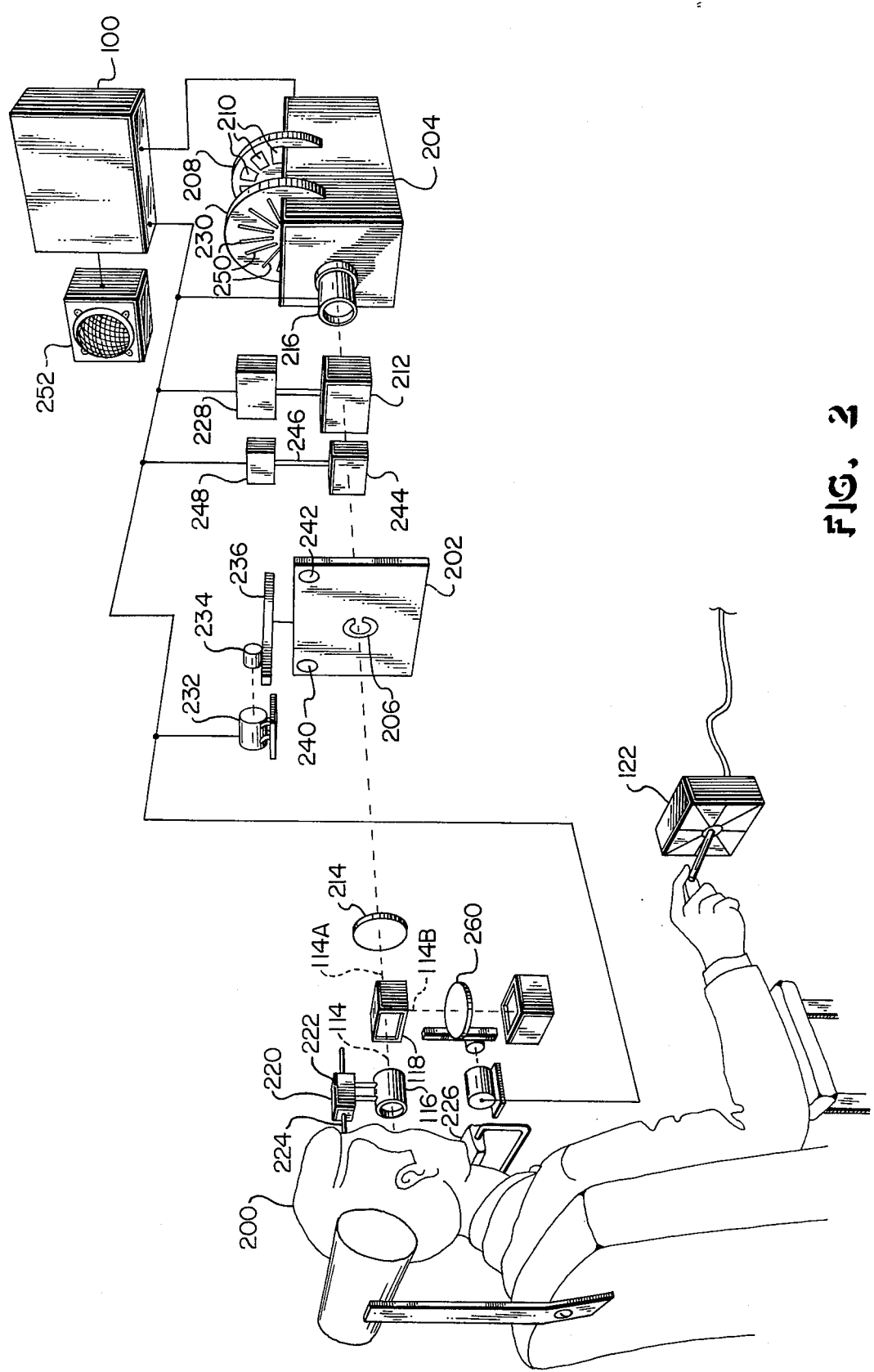
FIG. 2 is a perspective view illustrating the general arrangement of the various elements of one illustrative embodiment of the invention.

Referring to FIG. 2, there is shown illustrative apparatus for automatically measuring refractive error of the eyes of a subject 200. Test symbols and other visual stimuli are presented to the subject under control of a programmed automatic data processor or computer 100. The subject views the test symbols through an optical system, also controlled by the processor 100 and communicates responses to the processor. The subject is automatically given instructions as the examination proceeds so that no human intervention is necessary once the examination is underway.

The subject 200 is positioned a predetermined distance from a test screen 202 on which test letters or symbols are displayed for viewing by the subject. A projector 204 operates under control of the processor 100 to project test symbols on the screen 202. The test symbols used might be any of the standard symbols used in performing eye examinations. For example, the symbol 206 shown on the screen 202 is the so-called Landoldt ring. This symbol consists of a ring with an opening or break in one of eight locations about the ring —either in the upper part of the ring, the upper right hand part, the right hand part, etc. The Landoldt ring symbol is commonly used in performing subjective visual acuity tests. The symbol is displayed and then the subject is asked to indicate where the opening or break in the ring is located. The accuracy of the responses of the subject to the presentation of different size Landoldt rings provides a measure of the subject's visual acuity.

The use of the Landoldt ring symbol is especially advantageous in the present invention since a relatively simple manual response device 122 may be used to enable the subject 200 to communicate his responses to the processor 100. The manual response device 122 is situated within convenient reach of subject 200 so that during the course of the eye examination, the subject may operate the response device 122 with his hand. The use of the manual response device 122 will be discussed in greater detail later.

The projector 204 includes a rotatable wheel 208 which holds a plurality of transparencies or slides 210 containing different size symbol images. The processor 100 signals the projector 204 to cause it to rotate the wheel 208 to display symbols of selected size on the screen 202. As will be discussed later, a dove prisms 212 is provided for rotating the projected symbols so that the break in the ring may be positioned in any one of the above-defined eight locations. Rotation and positioning of the symbols is also carried out under control of the processor 100.

The subject 200 views the test symbols presented on the screen 202 through a lens system included in a lens system housing (not shown) supported by a suitable floor or wall support (not shown). The housing also contains the objective refraction system 124. The lens system includes variable crossed cylinders 116 positioned immediately in front of the subject's right eye, beam splitter 118 positioned in front of variable crossed cylinders 116, and a fixed positive power lens 214 positioned between the beam splitter 118 and the screen 202. (Although not shown in the drawing, the lens system includes a second variable crossed cylinder, beam splitter and fixed lens which are positioned in front of the left eye of the subject during the examination).

Variable crossed cylinders 116 are used in determining astigmatic error. Various crossed cylinders 116 consist of two cylindrical lenses of equal power but opposite sign, i.e. one is a plus cylinder and the other is a minus cylinder. The cylinders are positioned one in front of the other in a housing and in the pathway of the direction of gaze of the subject so that the axes of the cylinders are perpendicular to the direction of gaze. The cylinders are rotatable with respect to each other so that the angle between the axes thereof may be varied—it is for this reason that the cylinders are known as variable cross cylinders. Because the powers of the two cylinders are equal but opposite in sign, when the axes of the cylinders are aligned (parallel) the cylinders cancel each other so that the power of the combination is zero; when the axes are 90° apart, the combination has a maximum positive cylindrical power along the plus cylinder axis and a maximum negative cylindrical power along the minus cylinder axis. As is well known in the refractive art, by varying the angle between the axes of the variable crossed cylinder system (which are always 90° from one another in any cylindrical lens or lens system) and the cylindrical power of the system vary in a predictable manner. Specifically, the plus axis of the combined system is located exactly 45° from a line bisecting the axes of the individual plus and minus cylinders in a direction the axes of the individual plus and minus cylinders in a direction toward the axis of the plus cylinder. As already indicated, the location of the minus axis of the combined system is 90° from the plus axis of the system. The cylindrical power along the plus axis of the variable crossed cylinder combination varies from zero to a positive maximum and the cylindrical power along the minus axis of the combination varies from zero to a negative maximum.

With proper rotational positioning of the variable crossed cylinder, the power and axis necessary to correct astigmatic error can be determined. One such test for determining the required astigmatic correction will be described later when discussing an exemplary method of utilizing the FIG. 4 apparatus.

As previously described, present methods of subjective refraction include the use of different power lenses sequentially placed in position in front of the subject's eye. This may be accomplished by providing a plurality of lenses arranged in a multi-layered turret assembly wherein a wide variation in lens power may be achieved by rotating the proper combination of lenses to be positioned in front of the subject's eye. However, such a system has a disadvantage of being rather bulky and cumbersome. An improved aspect of the present invention utilizes the basic principle that the further a positive power lens is from the eye, the more positive it seems to be. Using the combination of fixed positive lens 214 and moveable rear projection screen 202, a full range of plus and minus spherical powers may be obtained. This may be written as follows: For a lens which has the power $D_L = 1/F$, where F is the focal length of the lens, $F_i$ is the distance from the lens to the image, and $F_o$ is the distance from the lens to the object itself:

$$\frac{1}{f_i} + \frac{1}{f_o} = D_L$$

$$\frac{1}{f_i} = D_E \text{(effective power)}$$

Therefore, $D_E = D_L - \frac{1}{f_o}$

Thus, for $f_o < F = > D_E < O$
$f_o = F = > D_E = O$ (plano)
$f_o > F = > D_E > O$ Thus, if the image on the rear projection screen 202 is maintained in focus, moving the screen along optical path 114A can effectively vary the spherical power of the system. Of course, by moving the screen 202 either toward or away from the fixed lens 214, the size of the projected symbol 206 is varied. When a test symbol (which could be but need not be the Landoldt ring symbol) is to be presented on the screen and the subject is to view the symbol through the optical system set alternately at two different powers, it is desirable that the apparent size of the symbol remain constant to the subject so that when called upon to indicate a preference between the two power settings, he will not be influenced by any apparent change in the size of the symbol. Therefore, to compensate for the size change of the symbol due to the position of screen 202, the position of the screen 202 and the zoom of the lens system 216 of projector 204 may be mechanically interlocked via a cam system (not shown). Additionally, the position of screen 202 and the focus mechanism of lens system 216 of projector 204 may also be mechanically interlocked vial a cam system (not shown). An exemplary system of interlocks is employed by the Omega photographic enlargers. It is obvious this may be accomplished alternatively by a variety of electrical means such as direct computer control, etc.

The variable crossed cylinders 116 are attached to vertex distance measuring apparatus 220. As fully described in U.S. Pat. No. 3,904,280, the vertex distance measuring apparatus 220 provides for determining the so-called vertex distance — the distance between the cornea of the subject's eye and the surface of the lens nearest the subject (in this case the variable crossed cylinders 116). Since the power of a trial lens system needed to correct refractive error depends in part upon the vertex distance, it is important to either maintain the vertex distance constant throughout an eye examination or to take into account in conducting the examination any vertex distance changes which occur during the examination. As fully described in the aforementioned patent, the apparatus 220 may be used either in maintaining a constant vertex distance or in detecting any changes in the vertex distance.

The apparatus 220 includes a housing 222 and a feeler bar 224 slidable in the housing. The feeler bar 224 contacts the forehead of the subject 200 to either detect movement of the subject's forehead toward or away from the apparatus or to prevent movement of the subject's head. In the latter case, after the apparatus has been used to measure the vertex distance, the feeler bar 224 is locked in place against the subject's forehead so that movement of the subject's forehead toward the apparatus 220 is prevented. (A chin rest 226 is also provided to stabilize the vertex distance). In the former case, any movement of the forehead of the subject 200 causes a corresponding movement of the feeler bar 224 within the housing 222 and this movement causes the generation of a signal which is transmitted to the processor 100. The polarity and magnitude of the signal indicate the direction of movement of the subject and the magnitude of such movement respectively. In response to the signal, the processor 100 automatically causes appropriate adjustment in the optical system to compensate for the change in the vertex distance.

As described earlier, visual acuity may be measured by presenting Landoldt ring symbols to the subject and then eliciting from the subject a response as to the location of the break or opening in the rings. As also discussed earlier, dove prism 212 may be rotated by its associated servo 228 under control of processor 100 to angularly position the ring opening. The Landoldt ring symbols are contained in transparencies 210 of wheel 208 which is inserted in projector 204. Each of the transparencies 210 includes a different size Landoldt ring symbol. (Wheel 230 is used in the OKN test and contains a clear window containing a minus lens, which is placed in the optical path of projector 204 when the Landoldt ring symbol test is utilized. The use of wheel 230 will be described in more detail hereinafter.) Processor 100 controls projector 204 to rotate the proper size Landoldt ring symbol transparency 210 on wheel 208 into the optical path of the projector. Processor 100 also controls servo 232 which is coupled to wheel 234 connected to rack 236 to position screen 202 for the proper power of the optical system. Also, lens system 216 of projector 204 is controlled by processor 100 to maintain the symbol projected on rear projection screen 202 in focus and to control the size of the projected symbol to compensate for variation in the power of the optical system. That is, when a test symbol, (which could be but need not be the Landoldt ring symbol) of fixed size is to be presented on screen 202 and the subject is to view the symbol through the optical system set alternately at two different powers, it is desirable that the apparent size of the symbol remain constant to the subject so that when called upon to indicate a preference between the two power settings, he will not be influenced by any apparent change in the size of the symbol. At this point, it should be noted that whereas a rear projection screen 202 has been depicted in FIG. 2, it may be desirable to eliminate the screen 202 and form a virtual image of the test symbol in the air at the plane at which the screen would have been positioned. This option may permit the repositioning or elimination of lens 214. This alternative provides the advantage that the projection system may be made more compact by using mirrors which may or may not be part of the focusing arrangement of the optical system to fold and thereby shorten the optical path. Moreover, this removes any physical constraints on the location of the image, which could, for example, be (theoretically) located behind the subject's head, an obvious impossibility with a screen. This also has the advantage of mechanical simplicity, since the screen with its required mechanical and electronic accessories is eliminated. However, for purposes of illustration and simplicity, the discussion will proceed on the basis that a rear projection screen 202 is utilized.

Various alternatives are contemplated to reduce confusion in eliciting power preferences from the subject. One such alternative is the use of a pair of lights 240 and 242 mounted on screen 202, or elsewhere, which are alternately lit to indicate a different power setting of the optical system. For example, light 240 may be lit when power setting 1 is chosen by processor 100, and light 242 may be lit when power setting 2 is chosen by processor 100. The subject may then be asked to express a preference for the power settings by moving his manual response unit 122 to the left to indicate a preference for power setting 1 or the right to indicate a preference for power setting 2. To further reduce confusion, the lights 240 and 242 may be of different colors, for example light 240 may be green and light 242 red.

A further alternative might be to include a prism 244 positioned in the pathway of the projected symbol and rotatable about a vertical axis between two positions for causing the projected symbols to appear at either of two horizontally spaced locations on the screen 202. When the subject 200 is requested to indicate a preference for one of two power settings of the lens system, the symbol is projected at one location for one of the power settings and the other location for the other power setting. The subject 200 then need only indicate the location of the "preferred" symbol, i.e. indicate the leftmost location or the rightmost location. The prism 244 is mounted on a vertical shaft 246 which in turn is rotatably driven by servo 248 under control of processor 100. When processor 100 changes the optical system power setting in the course of eliciting responses from subject 200, it also signals servo motor 248 to rotate the shaft 246 and thus the prism 244 to cause the projected symbol to move between the two locations on the screen. The locations on the screen at which the symbol appears are spaced reasonably close together (e.g., 6 inches) so that the symbol when presented in either location is well within the field of view of the subject looking through the optical system.

Rather than program the processor 100 to automatically change the location of the projected symbol and the power setting of the optical system so that the subject 200 must involuntarily change his direction of gaze to enable him to view the symbol, it may be desirable to allow the subject to alternately view two spaced, simultaneously presented symbols at his choosing, and to automatically change the power setting of the trial lens when the subject's direction of gaze changes. A simple beam splitting prism (not shown but which may take the place of prism 244) could be positioned in the symbol image pathway to cause the image to be projected simultaneously at the two locations on the screen 202. The direction of gaze of the subject is then monitored by eye movement monitor 126 so that when his gaze moves from one of the locations on the screen toward the other location, the processor 100 automatically causes the optical system to change power settings. Similarly, when the gaze of the subject moves back toward the first mentioned locations, the processor 100 automatically returns the power setting of optical system to the first mentioned setting.

A number of arrangements may be provided for monitoring a subject's direction of gaze including a device known as an electro-oculograph monitor diagrammatically illustrated in FIG. 3. The technique of electro-oculography is based on the fact that a D.C. potential difference exists between the corneal surface (at the front of the eye) and the posterior vascular layer of the eyeball. This potential is known as the corneal-retinal standing potential and is illustrated in a schematic manner in FIG. 3 which shows the corneal portion 310 of the eyeball having a positive potential with respect to the posterior or retinal portion 314. This standing potential varies from person to person somewhat but has been observed to be as great as one millivolt in some individuals and as small as 0.30 millivolts in others. Electrodes 302 and 306, situated as shown in FIG. 3, can be used to monitor eye movements in a horizontal plane by measuring variations in the electric field surrounding the eye produced by the corneal-retinal standing potential. For example, suppose that the eyeballs illustrated schematically in FIG. 3 rotate in a horizontal plane in the direction indicated by arrows 318 and 322 through the angle $\alpha$. This would bring the positive corneal surfaces of the eyes closer to electrode 306 and similarly bring the negative posterior regions closer to electrode 302. This would increase the potential difference between the two electrodes from its initial value before the eye movement. The algebraic sign of the movement is also indicated by the direction of the potential difference change as measured at the electrodes. A more complete discussion of the voltage produced by eye movement is found in U.S. Pat. No. 3,833,235. A D.C. amplifier 326 is used to amplify the relatively small voltage difference produced with eye movement and the resultant output is supplied to the processor 100. This output will be either positive or negative depending upon the direction of the eye movement.

The electrodes 302 and 306 used to measure the eye position could be placed on some type of face mask worn by the subject or alternatively could be attached to the subject's skin by adhesives and connected to the remainder of the system by flexible leads. In either case, it is desirable to have good skin-electrode contact as the voltages being measured are relatively small.

Using the electro-oculograph monitor 126 of FIG. 3 with the FIG. 2 system, the processor 100 may be programmed to respond to a change in the direction of gaze of subject 200 by changing the power setting of the optical system.

The system of FIG. 2 also includes a wheel 230 inserted in projector 204 which operates under control of the processor 100. The wheel 230 comprises a plurality of radially extending transparent slits 250 alternating with opaque areas which is controlled by the processor 100 to display horizontally moving vertical black and white bars on screen 202. Recall, that one type of objective examination for testing visual acuity is the OKN test in which the reflex "following movement" of the eye is monitored as vertical bars are moved horizontally in front of the eye. In the system of FIG. 2, the processor 100 causes the projector 204 to place an open frame of wheel 208 in the optical path inside the projector and then to rotate wheel 230. Details of how this is accomplished will be set forth hereinafter. Projector lens system 216 controls the magnification and focus of the image of screen 202 so that horizontally moving vertical bars of a predetermined width are presented on screen 202 and the subject is instructed to view the moving bars through optical system. Depending upon the visual acuity of the subject when looking through the optical system and upon the width of the bars, the subject will either exhibit the reflex "following movement" by following the movement of the bars or he will not. The previously described electro-oculograph monitor detects any movement of the subject"s eye and provided a signal indication to the processor 100 of the eye movement. As will be discussed more fully later, the OKN test is advantageously used at various points throughout an eye examination to provide information as to selection of lens system powers to present to the subject. Use of the OKN test in conjunction with the "subjective refinement" test requiring a conscious response by the subject facilitates rapid and accurate determination of the subject"s refractive error.

In order to provide a completely automated system and eliminate the need for human intervention in the examination process, it is necessary that provision be made for automatically giving instruction to the subject. This is done in the FIG. 2 system by providing tape player and control unit 252 which, just as in the case of the other apparatus of FIG. 2, operates under control of the processor 100. The tape player is provided with one or more tapes contaning pre-recorded messages of instruction. These messages are recorded at predetermined and known locations on the tape so that when a particular message is to be given to the subject 200, the processor 100 simply signals the tape player 252 to position the tape at the desired location, and then signals the tape player to operate to reproduce the desired message. Exemplary messages might include instructions as to how to use the manual response device 122, instructions on selecting preferences between successively displayed symbols, instructions on viewing the screen 202 on which the symbols are projected, etc. Computer control of tape or other recording devices is well known.

Referring now to FIG. 4, depicted therein is a block diagram of an objective refraction system which may be utilized in accordance with the teachings of this invention. The variable crossed cylinders 116 comprises two cylinders 402 and 404 which are rotatably driven by respective servo motors 406 and 408. The motors 406 and 408 operate under control of control unit 100. Since variable crossed cylinders 116 are between eye 112 and beam splitter 118, the variable crossed cylinder are part of both the objective and subjective refraction systems and one setting of variable crossed cylinders 116 sets the cylindrical power for both systems. In order to maintain the refractive power the same for both the objective and subjective refractive systems, the position of lens 260 is controlled by rack and pinion 410 which is coupled to servo motor 412 which in turn is under the control of processor 100.

Objective refraction measurements are made utilizing moving grid generator 412 which is optically coupled to eye 112 through dove prism 416, focusing lens 418, beam splitter 420, lens 260, beam splitter 118, and variable crossed cylinders 116. The purpose of moving grid generator 414 is to project on to the retina of eye 112 a pattern of alternating dark and light bars which may be utilized by objective refraction analyzer 422, in a manner to be described hereinafter. Moving grid generator 414 may take any of various forms. For example, moving grid generator 414 may comprise a light source inside a rotating "carousel" wheel, the periphery of the wheel being alternately opqaue and transparent. Alternatively, moving grid generator 414 may comprise a light source adjacent a vibrating reed, a moving fiber optic bundle or similar devices. The particular form of moving grid generator 414 is not an aspect of the present invention.

The grid pattern on the retina of eye 112 is electrically coupled to objective refraction analyzer 422 by means of a pair of photoconductive devices 424 and 426 which may be, for example, phototransistors, photodiodes or photocells. Photoconductors 422 and 46 "see" the moving grid pattern on the retina of eye 112 through dove prism 428, focusing lens 430, beam splitter 420, lens 260, beam splitter 118, and variable crossed cylinders 116. The operation of objective refraction analyzer 422 will be described in more detail hereinafter with respect to the description of FIG. 5B.

Dove prisms 416 and 428 are both controlled by servo motor 432. Dove prisms 416 and 428 are utilized when measuring the cylindrical refraction utilizing the method of meridional refractometry, so as to get objective refraction measurements at different meridia, to be described in more detail hereinafter with reference to FIG. 8A.

Figure 5A:
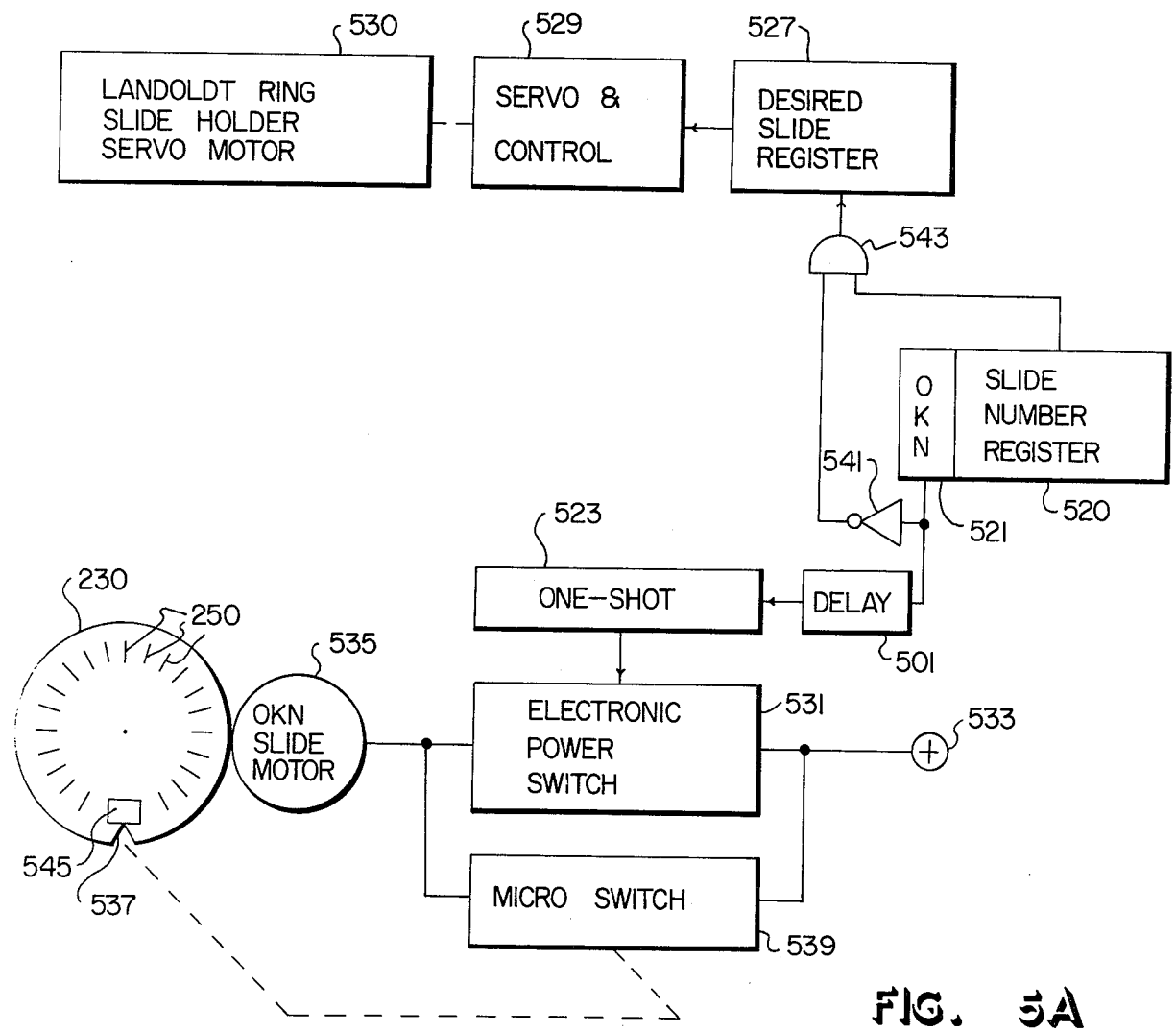
Figure 5B:
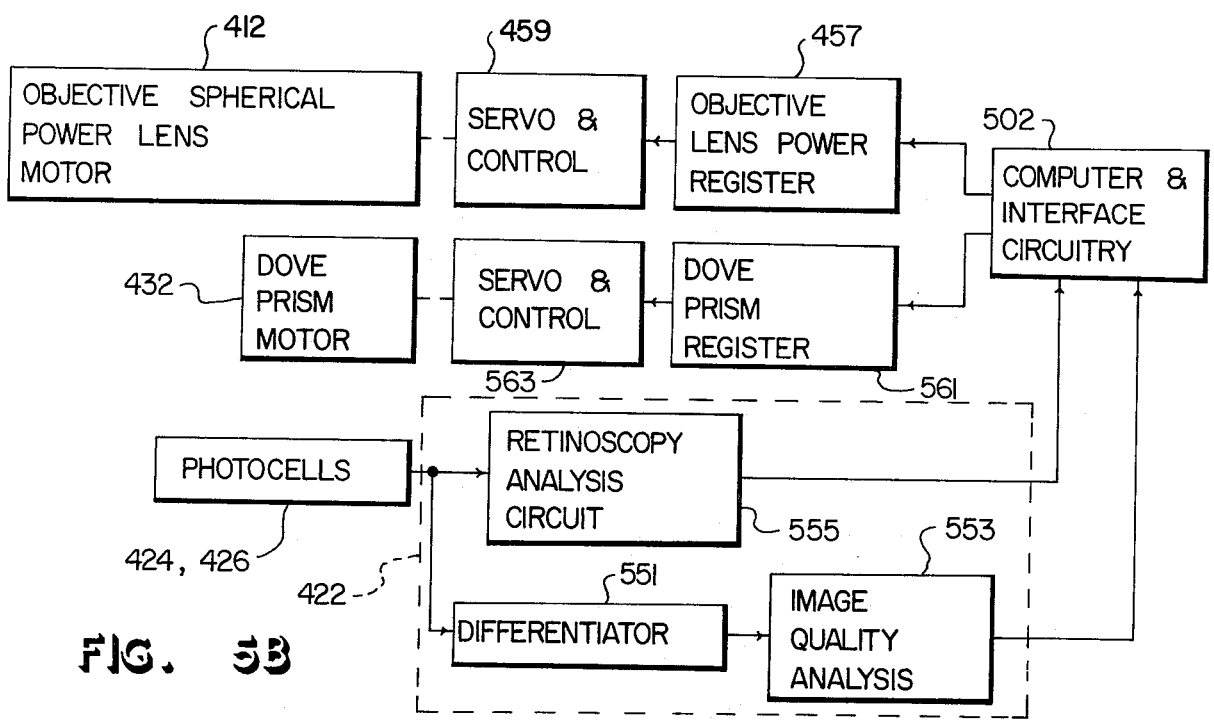

In FIG. 5, 5A, and 5B the overall system of one embodiment of the present invention is shown in block diagram form. The automatic data processor 100 of FIG. 1 is represented in FIG. 5 by computer and interface circuitry 502 and a memory 504 coupled to the computer. The computer 502 may be any one of a number of available general purpose computers or a special purpose hardwired machine. For example, the computer 502 could illustratively be the PDP-11 made by Digital Equipment Corporation.

The computer 502 communicates with the external world and to the subject 200 via a plurality of external devices. Input information and especially initializing data is supplied by way of input circuits 508 which may comprise any of a variety of input devices such as a tape reader, card reader, typewriter, etc. Such input data indicates the initial settings to be made by the computer 502 of the various items of equipment. The computer 502 communicates with the system operator through the use of output circuits 510. These circuits may comprise any of a variety of computer output displays or recording devices such as a cathode ray tube, a line printer, a typewriter, or other desired device capable of converting the computer output to a form usable by the operator. The memory 504 stores data which is to be processed by the computer 502 and also the programs which control the operation of the computer.

Output signals or commands are supplied by the computer 502 via a plurality of data lines to the external testing equipment. Signals for controlling the operation of the projection apparatus are supplied via lines 512 to various data registers 514, 516, 518 and 520. For example, digital information designating the angular position of the slide holder 208 (FIG. 2) is supplied by the computer 502 to a slide number register 520. This information designates to which angular position the slide holder 208 is to be rotated and thus which size symbol is to be projected onto the screen for viewing by the subject. This information is supplied to a slide unit 528 which responds by controlling the angular positioning of a slide holder motor 530, to be described later with respect to FIG. 5A. Other registers used in cotrolling the projection apparatus include the symbol size compensation register 514 for receiving digital information designating the magnitude of the size compensation to be made in the projected symbol (to compensate for variations in apparent symbol size due to optical system power changes), a symbol orientation register 516 for receiving digital information designating the angular positioning of the displayed Landoldt ring symbol, and a symbol position register 518 for receiving digital information designating the location at which the test symbol is to be displayed, if such is utilized in practicing the teachings of this invention. Corresponding servo and control units 522, 524 and 526 respond to such digital information by controlling the operation of corresponding servo motors 532, 228 and 248 (the latter two numerical designations are employed to indicate that the dove prism motor 228 is the same as the motor 228 of FIG. 2 and the position prism motor 248 is the same as the motor 248 in FIG. 2). The servo and control units 522, 524 and 526 are identical in construction and are shown in detail in FIG. 6.

Figure 6:
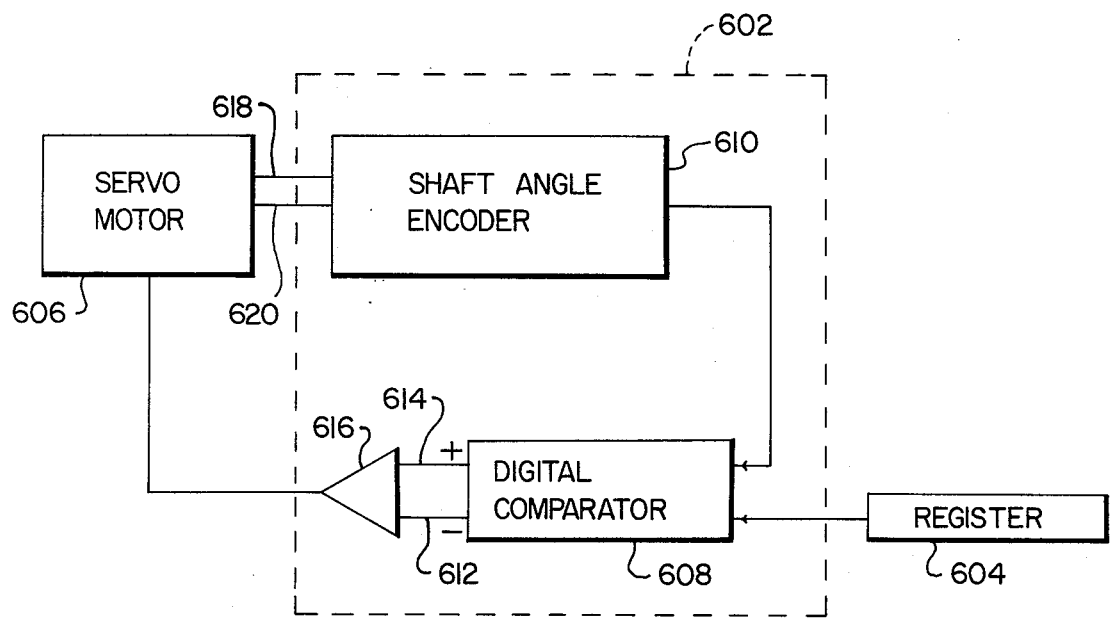
FIG. 6 is a block diagram of a servo and control unit.

A servo and control unit is shown in the dashed line rectangular box 602 of FIG. 6 connected to a register 604, from which digital information is received and to a servo motor 606 which is controlled by the unit 602. The information from the register 604 is applied to a digital comparator 608 and compraed with digital information received from a shaft angle encoder 610. The information from the shaft angle encoder 610 identifies the angular position of the drive shaft of the servo motor 606. If the angular position of the shaft of the servo motor 606 is the same as that designated by the information received from the register 604, then the digital comparator 608 produces no output signal. If the position of the drive shaft of the servo motor 606 is at an angle greater than that indicated by the information from register 604, then a signal is provided via lead 612 to an operational amplifier 616 which causes the servo motor 606 to reduce the angular position of its drive shaft by an amount indicated by the signal applied to lead 612. If the angular position of the drive shaft of the servo motor 606 is less than that indicated by the information from register 604, then the digital comparator 608 provides a asignal via lead 614 to the operation amplifier 616 which causes the servo motor 606 to increase the angular position of its shaft. In this manner, digital information is used to control the angular position of the drive shaft of a servo motor. Connection 618 between the servo motor 606 and the shaft angle encoder 610 designates a mechanical connection to the drive shaft of the servo motor and connection 620 designates an electrical connection. The structure and operation of servo and control units such as that of FIG. 6 are well known in the art.

Referring again to FIG. 5, the dashed lined box 540 represents a protion of the subjective optical system used for testing the right eye of the subject. Included is a spherical power register 542 for receiving digital information designating the desired speherical power of the optical system and a pair of crossed cylinder registers 544 for receiving information designating the position of the variable crossed cylinders bylinders 402 and 404. This information is received from the computer 502. The information in the sperical power register 542 is supplied to servo and control unit 546 which controls the screen motor 232. Additionally, the information in spherical power register 542 is supplied to servo and control unit 547 which controls projector focus motor 548. It has been previously stated that an alternative embodiment would consist of only one servo with screen position and focus mechanically linked. The information in crossed cylinder registers 544 is supplied to servo and control unit 549 which controls cylinder motors 406 and 408. Servo and control units 546, 547 and 549 operate in the same manner as that described for the servo and control unit of FIG. 6.

The dashed line box 560 includes apparatus similar to that of the box 540 for use in the testing the left eye of the subject.

Referring now to FIG. 5A, the operation of slide control 528 which controls the projection onto screen 202 will now be described. Computer 502 supplies to slide number register 520 a digital word representing which of the transparencies 210 of slide wheel 208 is to be displayed or alternatively that the OKN test utilizing wheen 230 is to be conducted. A single bit position 521 in slide number register 520 is utilized to discriminate between the use of slide wheel 208 or OKN slide wheel 230. Assuming for the moment that bit position 521 is set to a ONE, this indicates that the OKN test is to be conducted. When bit position 521 is set to a ONE, this triggers one-shot circuit 523, through delay circuit 501, which puts an output pulse on lead 525. With a ONE in bit position 521, the output of inverter 541 is a ZERO. Therefore, an address of all ZEROS is gated through AND gate 543 into desired slide register 527. This causes servo and control 529 to operate the Landoldt ring slide holder servo motor 530 to rotate slide 208 so that a clear one of the windows 210 is in the optical path of projector 204. The purpose of delay circuit 501 is to insure that the foregoing operation is completed before a pulse is applied to lead 525. The pulse on lead 525 is applied to electronic power switch 531 which momentarily applies power from source 533 to OKN slide motor 535, which is illustratively shown as being frictionally engaged with the periphery of OKN slide wheel 230. This causes OKN slide wheel 230 to begin to rotate. OKN slide wheel 230 is designed with a notch 537 cut therein. Microswitch 539 is mechanically linked to OKN slide wheel 230 so that when microswitch 539 is in notch 537, switch 539 is open and when microswitch 539 is against the outer periphery of slide wheel 230, switch 539 is closed. Therefore, as slide wheel 230 rotates and switch 539 comes out of notch 537, switch 539 closes a path between power supply 533 and OKN slide motor 535. In the meantime, electronic power switch 531 has opened. Power is therefore supplied to OKN slide motor 535 until OKN slide 230 makes one full revolution, at which point microswitch 539 is again in notch 537 and is opened. Thus, in summary, when computer 502 indicates, by placing a ONE in bit position 521 of slide number register 520, that the OKN test is to be run, Landoldt ring slide holder 208 is rotated to a clear window position and then OKN slide wheel 230 is caused to make one revolution. During that single revolution of slideholder 230, a pattern of moving bars is projected onto screen 202 because transparent slits 250 alternating with opaque areas of slide wheel 230 pass through the optical path of projector 204.

When computer 502 determines that a Landoldt ring symbol is to be projected onto screen 202, the symbol number is placed in slide number register 521 with a ZERO bit being placed in bit position 521. This ZERO in bit position 521 is inverted by invertor 541 to enable AND gate 543 which allows the slide number in slide number register 520 to be gated into desired slide register 527. Servo and control 529 utilizes the address in desired slide register 527 to control Landoldt ring slide holder servo motor 530 to place the proper one of the transparencies 210 in the projection path of projector 204. At this time, OKN test wheel 230 is at its rest position with microswitch 539 being in notch 537. In this position, a clear window containing a minus lens 545 in OKN wheel 230 is in the projection path of projector 204 so that only the proper Landoldt ring is displayed on screen 202.

It is to be noted that for the sake of simplification additional leads, such as timing or strobe leads for the various registers, have not been shown.

In FIG. 5B there is depicted the objective system control and analysis circuitry 570 for controlling the objective refraction portion of the disclosed system, as shown in FIG. 4. There are two aspects to vision. One is purely resolution, the other image quality. Resolution corresponds to the ophthalmic concept of visual acuity, whereas a poor image quality would correspond to situations where the visual acuity remains good, but the view is nonetheless described as "hazy" or some similar term. Two optical systems may have the same limiting resolution yet transmit contrast differently. The basic concept is that the contrast transmission of a lens as a function of spatial frequency of the target is dependent upon the line spread function of the lens. The concept of the line spread function basically is the way a point source is imaged by the lens system. This contrast transmission function may either be expressed as a modulation transfer function or as an image energy distribution function. Although a detailed discussion is outside the scope of this application, the important point is that optical quality is related to contrast transmission at higher frequencies. For the purposes of this application, the imaging of a square wave provides us with sufficient information. A detailed description of the modulation transfer function is given in the book *Modern Optical Engineering* by W. J. Smith, McGraw Hill (1966, Pages 308 through 325.

From a mathematical analysis, it is known that a square wave has an infinite frequency content of odd harmonics. This may be shown by generating a Fourier expansion of the square wave. The multipliers in the square wave expansion are a constant multiplied by the reciprocal of the harmonic. These coefficients of each term of the square wave as imaged are multiplied by a second group of coefficients which are derivable from the value of the modulation transfer function at the particular harmonic frequency. By differentiating the expansion series for the image, the divisor is eliminated and the multiplier is simply a fixed multiple of the value of the modulation transfer functions for that harmonic. Thus, the relative maxima of this series relate to the optical quality of the optical system. Thus, when moving grid generator 414 images the analog of a square wave on the retina of eye 112, if vision were perfect, the output of photocells 424 and 426 would be a perfect square wave. Differentiator 551 is connected to receive the output of one of the photocells 424 or 426 and differentiate the signal therefrom. Image quality analysis circuit 553 can then provide to computer 502 a signal representative of the image quality, as determined by the level of the output of differentiator 551.

Retinoscopy analysis circuit 555 is coupled to the output of both photocells 424 and 426. Retinoscopy analysis circuit 555 may be any of several well-known objective refractors, one such being that described in U.S. Pat. No. 3,136,839 issued to Aran Safir on June 9, 1964 and entitled "Apparatus for Objectively Testing An Optical System". Computer 502 utilizes the output of retinoscopy analysis circuit 555 when making objective refraction measurements. It will be noted that the position of lens 260 (FIG. 4) will be in a different setting for the two functions of retinoscopy and image quality.

The power of the objective system is controlled by controlling motor 412 to move lens 260. This is accomplished by computer 502 putting the desired lens position information into objective lens power register 557. Servo and control 559 utilizes this information to control motor 412. When performing meridional refractometry, dove prisms 416 and 428 must be rotated under the control of motor 432. This is accomplished by computer 502 placing the desired angular position of the dove prisms into dove prism register 561. Servo and control 563 then utilizes this information to control dove prism motor 432.

Servo and control 529 (FIG. 5A) and servo and controls 559 and 563 (FIG. 5B) are all similar to that shown in FIG. 6.

A vertexometer 220, corresponding to the vertex distance measuring apparatus 220 of FIG. 2, is provided to detect movement of the head of the subject 200 and to signal the computer 502 accordingly. When such movement is detected by the vertexometer 220, indicating a change in the vertex distance, the computer 502 calculates the effect of such movement on the effective power of the optical system and signals the optical system equipment 540 and 560 to change the power by an amount sufficient to compensate for the movement.

A direction of gaze monitor 126, as also described earlier, is provided to perform two functions. One function is to detect whether or not the subject 200 exhibits the reflex "following movement" when the OKN test is being performed and to signal the computer 502 accordingly. The other function, as the name indicates, is to monitor the direction of gaze of the subject 200 when test symbols are being displayed at two locations on the test screen so that the power setting of the optical system can be changed when the direction of gaze of the subject 200 changes. The computer 502, in response to a signal from the direction of gaze monitor 126 indicating that the subject 200 has changed his direction of gaze, signals the optical system to make the appropriate change.

For those portions of the eye examination requiring a conscious response by the subject 200, a manual response device 122 is provided for communicating the subject's response to the computer 502. The manual response device 122, also known as a "joy stick", includes a finger 580 manually movable to "point" to any of the eight sectors indicated on the face of the device. Each of the eight sectors corresponds in position to one of the eight locations at which the opening or break in a Landoldt ring is found. Thus, when a Landoldt ring symbol is displayed for viewing by the subject, if system powers, subject is able to see the opening in the ring, he indicates its location by moving the finger 580 toward the sector corresponding to the location of the opening.

A signal indicating the sector or angular arc in which the finger 580 is positioned is applied to an encoding matrix 582 which encodes the signal into digital form and supplies it to a digital response register 584. The digital response register 584, in turn, may be sampled selectively by the computer 502 under program control. As will be explained later when describing an illustrative process for using the FIG. 1 and 5 system, the responses made by the subject are utilized by the computer 502 in determining what optical system powers, test symbols, etc., to next present to the subject.

The manual response device 122 is also used by the subject 200 to indicate a preference for one of a pair of test symbols presented on the screen. If the subject prefers the symbol presented first or in the left-most location on the screen, he moves the finger 580 to the left and if he prefers the symbol presented second or in the right-most location, he moves the finger 580 to the right. Again, the manual response device supplies a signal to the encoding matrix 582 indicating the direction in which the finger 580 was moved and this information is ultimately supplied to the computer 502.

Figure 7:
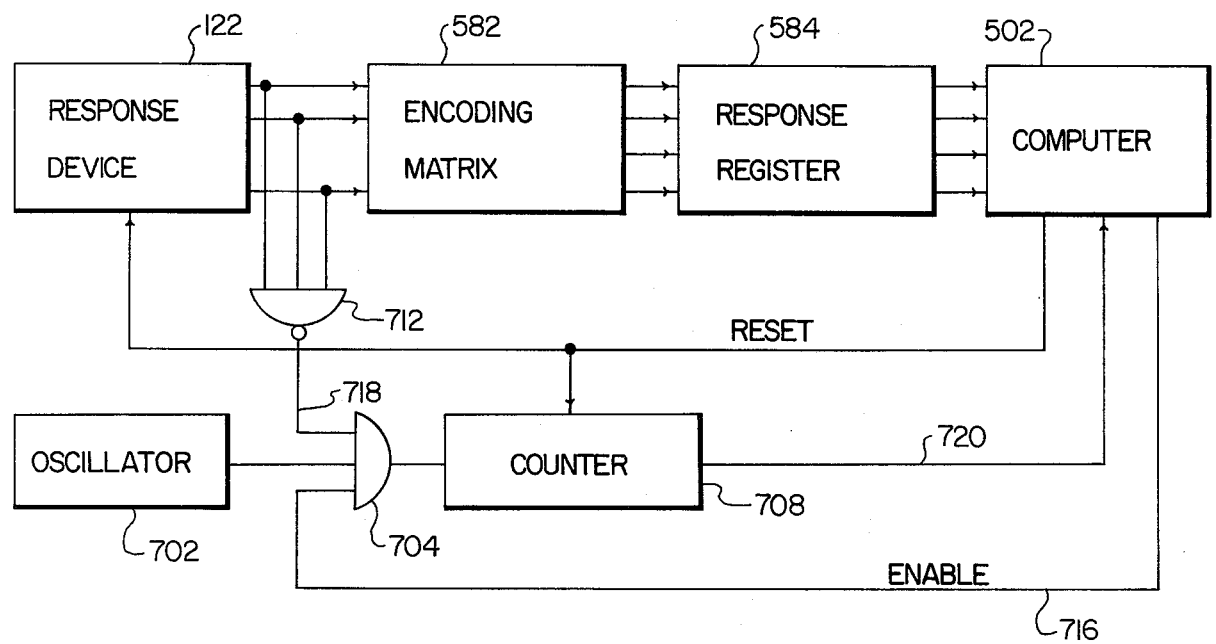
FIG. 7 is a block diagram of apparatus for measuring the response time of a subject.

Alternative manual response apparatus is shown in block diagram form in FIG. 7. With this apparatus, a measure of the time it takes the subject to respond to various test requests is made and this information is utilized by the computer 502 in determining subsequent optical system power choices, symbol sizes, etc., to present to the subject. The apparatus includes the previously discussed response device 122, encoding matrix 582, and response register 584 connected to a computer 502. Also included is an oscillator 702 whose output is coupled to an AND gate 704 which, in turn, is connected to a counter 708. The outputs of the response device 122 are coupled to a NAND gate 712 whose output is connected to the AND gate 704. A third input to the AND gate 704 is by way of a lead 716 from the computer 502. The oscillator 702 operates continually to supply a succession of output pulses to the AND gate 704.

When the computer 502 initiates a presentation of test symbols requiring a response from the subject, it applies an enable signal via lead 716 to the AND gate 704. Since, at this time, there would be no output from the response device 122, an output signal is generated by the NAND gate 712 and applied to the AND gate 704 via lead 718. Since signals are being applied to both leads 716 and 718, the pulses generated by the oscillator 702 will be applied via the AND gate 704 to the counter 708 causing the counter to commence counting, i.e., incrementing with each pulse. The counter 708 will continue to count until the AND gate 704 is disabled. This occurs when the response device 122 is operated so that an output signal is applied to at least one of the output leads of the response device causing the NAND gate 712 to terminate generation of an output signal. This results in the disablement of the AND gate 704. With the AND gate 704 disabled, no pulses from the oscillator 702 can reach the counter 708 so that the counter terminates counting.

If the counter 708 does not reach a certain count, i.e., does not "time out", before the subject expresses a preference by operating the response device 122, it is assumed that the subject did not find it difficult in making a choice of one of the alternatives presented to him. If, on the other hand, the counter 708 exceeds some predetermined count, i.e., "times out" before the subject makes a response, it is assumed that the subject had difficulty choosing between the alternatives presented to him and therefore that the alternatives are about equally acceptable. In this case, the computer determines when a "time out" occurs by comparing the output of the counter 708 (i.e., the count on the counter) with some threshold count supplied to the computer at the beginning of the examination. Since the reaction times of different subjects will generally be different, a threshold count might be determined for each subject tested by making a few "test runs" and then selecting a threshold count which takes into account the reaction time of the subject. An exemplary threshold count would be the subject's average reaction time, determined by the test runs, plus three times the standard deviation of the average (using, for example, the well-known normal distribution).

As will be discussed later, the action taken by the computer 502 after presentation of symbols requiring a response depends upon whether or not there was a time out. After the subject's response time has been measured, the computer 502 applies a reset pulse both to the response device 122 and to the counter 708 in preparation for the next subject response time measurement.

Instructions for guiding the subject 200 in using the manual response device 122 and generally in taking the examination are given by a tape player 590 (FIG. 5). The tape player 590 includes one or more tapes containing pre-recorded messages of instruction for the subject. When a particular message is to be given to the subject, the computer 502 applies a signal to a tape controller 592 identifying the desired message and the tape controller signals the tape player 590 to properly position the tape and reproduce the desired message.

As can be seen from the above discussion, very little if any human intervention is required in conducting an eye examination with the system of the present invention. Even if some human assistance is desired, it would be of a type which a trained technician could do relieving the ophthalmologist from much of the time consuming routine required with currently used methods. Such assistance might include, for example, instructing the subject as to where he is to sit, positioning the optical system with respect to the subject, and generally making the subject feel at ease.

An alternative to use of the manual response device 122 of FIG. 5 for indicating a preference between symbols, is a VER monitor 596. (It is shown in dashed-line boxes to indicate that it is an alternative to the manual response device 122.) The monitor 596 includes a plurality of electrodes 595 which are secured to the scalp of the subject 200 for detecting the electrical activity (signals) in the occipital lobe of the brain. The detected signals are amplified by the monitor 596 and applied to an analog to digital converter 597 which converts the signals to digital form. The digital signals are then supplied to a register 598 which is selectively sampled by the computer 502. These signals represent (in digital form) an electroencephalogram of the subject. The computer 502 processes the signals to determine the clarity and sharpness with which the subject was able to perceive the pairs of test symbols presented to the subject. The relation of the visual acuity of the subject to the amplitudes of these signals was described earlier. In this manner, an unconscious response by the subject 200 is detected by the VER monitor 596 and communicated to the computer 502.

In operation, the system of FIG. 5 is set in motion by the operator through the input circuits 508. These input circuits are utilized together with the programmed control of the computer 502 to cause the test equipment to generate test stimuli on the screen 202 (FIG. 2). These test stimuli are viewed through the optical system whose power is modified from time to time in accordance with responses and actions from the subject communicated to the computer 502 by the manual response device 122, the direction of gaze monitor 126, the vertexometer 220, and the VER monitor 596. The response or action of the subject is then dynamically used by the computer 502 in the selection of subsequent stimuli to present to the subject, in selecting the lens system power to present to the subject, and in making previously described compensation for changed testing conditions, e.g. change in vertex distance. When the testing is complete, as determined by the program, the computer 502 generates and applies output data to the output circuits 510 specifying the results of the test, including eye wear prescription and vertex distance.

Referring now to FIGS. 8A, 8B, 8C and 8D, the overall method of one embodiment implemented by the computer program of Computer 502 is illustrated in a flow chart. in that flow chart, whenever there is a reference to putting a prescription in the lens system, what is meant is that proper adjustment is made to the position of screen 202 and the focusing of projector lens system 216 in the subjective refraction system, as well as the proper positioning of lens 260 in the objective refraction system, along with adjustment of variable crossed cylinders 116. The first step in the program, as indicated by block 802 of FIG. 8A is to perform an objective refraction of the right eye with all lenses set at plano. This is done by performing an objective refraction in at least three meridia and calculating the spherical and cylindrical parts of the prescription by a method known as meridional refractometry. A description of the foregoing may be found in the article entitled "Meridional Refractometry" by Richard F. Brubaker, Robert D. Reinecke and Jack C. Copeland, published in the Archives of Opthalmology, Vol. 81, June 1969, pages 849 through 852. The basic operation consists of setting variable cross cylinders 116 to plano, and then measuring the refractive error in three meridia; 0°, 45°, 90°. From this, one can calculate the required corrective prescription, per the above cited article. The next step is to set variable crossed cylinders 116 to the calculated prescription and then remeasure the remaining cylindrical power. If any cylindrical power remains, the error and the corrective prescription may be calculated using vector analysis to obtain the original cylindrical power of the eye. See "Optics" by K. N. Ogel, Ed 2, Chas. Thomas 1968, p. 173 for method. A new corrective prescription may then be set into variable crossed cylinders 116 and another measurement taken. The foregoing steps continue until the cylindrical power is neutralized as perfectly as possible or until a predetermined number of measurements have been made. Effectively what has been done is that after the first measurement is made, the cylindrical power is objectively neutralized rather than calculated to home in on the final correction. This is indicated in FIG. 8A by blocks 804, 806, and 808. After the right eye is objectively refracted, the left eye is objectively refracted using the same technique, as indicated by blocks 810, 812, 814, and 816.

After both eyes have been objectively refracted, as indicated by Block 818, the prescription for both eyes is made 0.25 diopter more positive. An objective refraction is again made to see whether the objective refraction in either eye changed, as indicated by block 820. If the objective refraction in either eye did change, the next step is to see whether it only changed in one eye, per block 822. If the change was only in one eye, as indicated by block 824, the prescription of the eye that changed is increased by 0.25 diopter and the program returns to block 820. If the objective refraction in both eyes changed, the program returns to block 818. After it is found that the objective refraction did not change after making the additional 0.25 diopter addition to the prescription, as indicated by block 826, 0.25 diopter is subtracted from the prescription of both eyes. This amounts to relaxing the accommodation by "fogging".

As indicated in block 828, FIG. 8B, the final objective prescription has now been obtained. The next step is to determine whether or not only an objective refraction is desired, as indicated by block 830. If only an objective refraction for that patient is desired, the program is exited and the objective prescription is utilized for that patient. There are several types of patients for whom only an objective refraction would be desired. There are the patients from whom one could not elicit subjective responses. For example, small children are not amenable to subjective refraction techniques. Also, many mentally retarded or emotionally disturbed persons are not subjectively refractable.

If a person is to be subjectively refracted, the next step in the program, as indicated by block 832 of FIG. 8B, is to call the subprogram to test the visual acuity of the subject with the power setting then present in the optical system. This test is conducted in accordance with the subprogram whose flow chart is shown in FIG. 9A and 9B. This subprogram provides for testing the visual acuity of the subject utilizing Landoldt rings and the OKN test.

The power setting of the optical system at this stage of the process will be that corresponding to the final objective prescription indicated in block 828. The first step of the FIG. 9A subprogram, as indicated in block 902, is to determine whether or not the visual acuity of the subject had previously been tested in the examination and if so whether an OKN response had been elicited (i.e., whether the subject exhibited the above-described reflex "following movement"). If the visual acuity of the subject had not previously been tested, then, as indicated in block 904, a Landoldt ring test is performed. The subprogram for the Landoldt ring test is illustrated in FIG. 9B, the first step of which involves the selection of a test symbol size corresponding to the then current visual acuity measurement of the subject (block 950). Recall that one subjective test for determining the visual acuity of the subject involves the presentation to the subject of different size Landoldt ring symbols and determining for which size the subject is able to specify the location of the break in the ring. The particular size of the Landoldt ring symbol for which the subject is able to do this defines a visual acuity for the subject. In step 950 of FIG. 9B, the reverse of this is carried out in that the symbol size corresponding to the subject's current visual acuity (i.e., visual acuity with the current power setting of the optical system) is selected. After the appropriate symbol has been selected, the computer 502 causes the projection apparatus to successively display a series of randomly oriented symbols of the selected size as indicated by block 952. As each symbol is displayed, the subject is requested to indicate the location of the break in the ring. After a series of symbols has been presented, e.g. six, and the responses to such presentations recorded, the computer determines whether or not two thirds or more of the symbol orientations were correctly determined by the subject (block 954). If they were, the symbol size is decreased, for example, by an amount corresponding to the change in size of symbols from one line of the well-known Snellen chart to a next adjacent line (block 956) and the subprogram returns to block 952 where a series of symbols are again presented to the subject. If the subject did not determine at least two thirds of the symbol orientations correctly, then the subprogram of FIG. 9B moves to block 958. In block 958, the determination is made as to whether, just prior to the previous presentation of symbols, the symbol size had been decreased or increased. If it had been decreased, then the subprogram returns to block 906 of FIG. 9A, otherwise the subprogram moves to block 960 of FIG. 9B. In the step represented by block 960, a determination is made as to whether or not the symbol size is maximum and if it is, the subprogram sets visual acuity equal to 20/800 (block 961), then returns to block 906 of FIG. 9A; if it is not, the subprogram moves to block 962 where the symbol size is increased by an amount corresponding to a one-line change on the Snellen chart. After the increase in symbol size, then a series of such symbols are again presented to the subject as indicated in block 952 and the process is repeated. The visual acuity of the subject is determined in the Landoldt ring test of FIG. 9B by that size of a test symbol whose orientation the subject is just able to determine two thirds or more of the time. Each symbol size, as already indicated, defines a visual acuity measure.

In block 906 of FIG. 9A a determination is made as to whether the visual acuity determined by the Landoldt ring test is greater or less than 20/800. If it is less than that, then the subprogram of FIG. 9A return to block 834 of FIG. 8B, otherwise it moves to block 908 of FIG. 9A. As indicated by block 908, an OKN test is performed with the vertical bar width selected to correspond to one half the visual acuity of the subject determined in block 904. (Recall that in the OKN test, the bar width at which a subject exhibits the reflex "following movement" defines a certain visual acuity). The subject is requested to view the screen 202 and if the response is elicited, as determined by the direction of gaze monitor, the subprogram of FIG. 9A moves from block 910 to block 914 otherwise it moves to block 912. In the step represented by block 912, the computer sets a flag indicating that only the Landoldt ring test is to be used thereafter and not the OKN test. The subprogram then returns to block 834 of FIG. 8B. In the step represented by block 914 of FIG. 9A, the current visual acuity measure of the subject is set equal to that determined by the Landoldt ring test of block 904 and the subprogram moves to block 916.

Returning now to the decision block 902, if it had there been determined that the visual acuity of the subject had been tested and that an OKN response had been elicited, then the process would have moved to block 916. In block 916, the OKN bar width is set to correspond to the current visual acuity measure of the subject — either that existing upon entering the subprogram of FIG. 9A or that established in block 914. The OKN test is then performed as indicated in block 918 and a determination is made as to whether a response was elicited from the subject (block 920). If a response was elicited, the bar width is decreased (e.g.) by one half, (block 924) and the OKN test is again performed. This cycle continues until a bar width is selected which does not produce a response from the subject in which case the subprogram moves to block 922 where the bar width is increased, e.g. by one half, and then to block 926 where a determination is made as to whether or not the bar width is at its predetermined maximum. The process could also reach block 926 if the initial determination in block 920 had been "No". If the bar width is maximum, the visual acuity is set to 20/800 (block 931) and the process returns to block 834 of FIG. 8B, otherwise it moves to block 928 of FIG. 9A. In the step represented by block 928, a determination is made as to whether the bar width, just prior to the increase in the width in block 922, had been decreased and if it had, the process returns to block 834 of FIG. 8B. if it had not been decreased just prior, then the OKN test is again performed (block 918) and the previously described operation repeats. The purpose of the functions performed in blocks 918, 920, 922, 924, 926, and 928 is to determine the visual acuity of the subject using the OKN test with the trial lens system set at a certain power.

Returning once again to block 902 of FIG. 9A, if it is determined that the visual acuity of the subject has previously been tested but that no OKN response was elicited, then the process moves to block 930 where the Landoldt ring test is performed in accordance with the subprogram of FIG. 9B as previously described.

Figure 10:
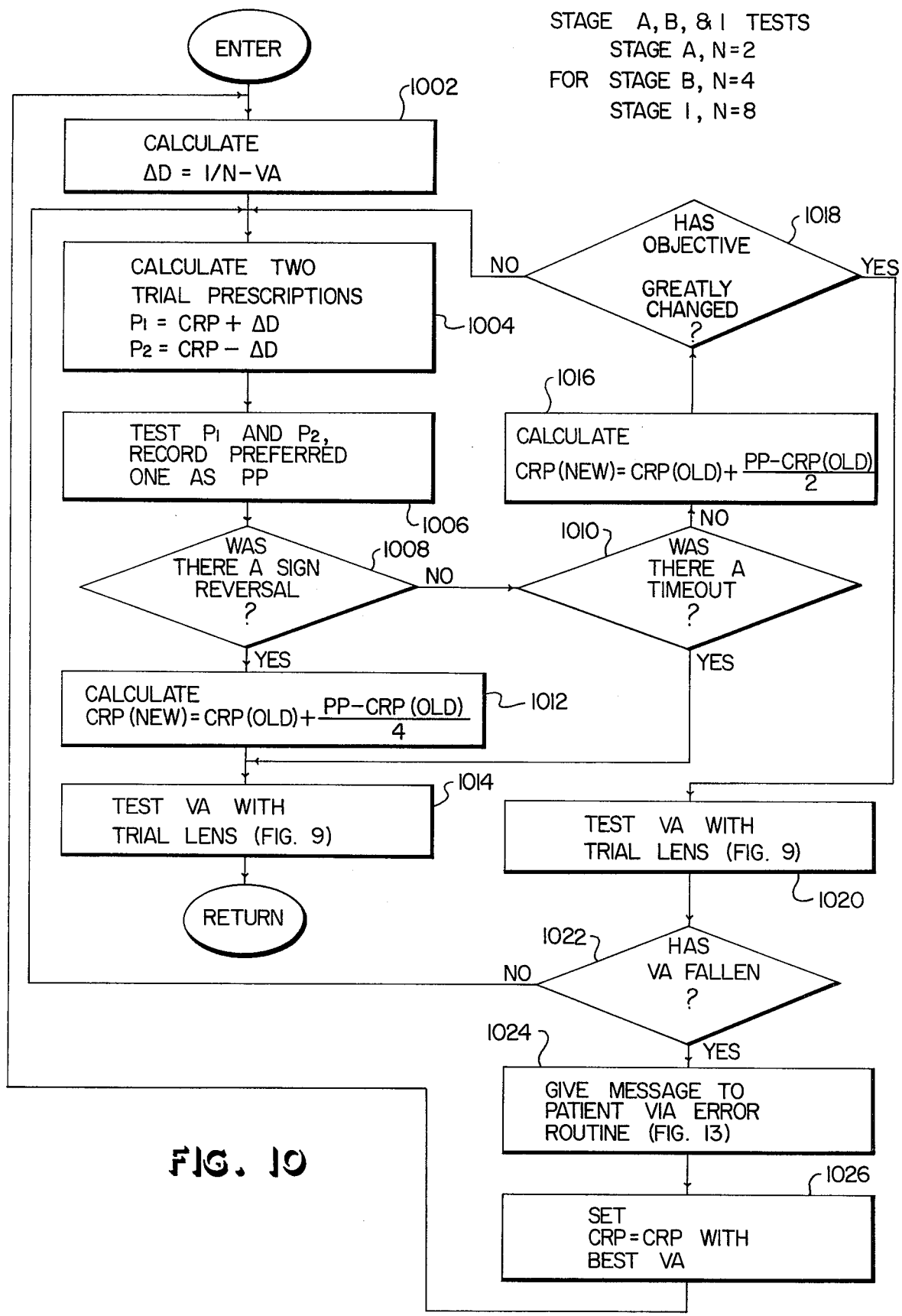

After block 832 of FIG. 8B is completed as indicated in FIGS. 9A and 9B, block 834 is to determine whether the visual acuity of the subject, based on the results obtained in block 832 is less than or greater than 20/80. If the visual acuity is less than 20/80, the program moves to block 836 where a socalled stage A rough test subprogram is called. This subprogram is illustrated in FIG. 10 which shows a general flow chart of three different subprograms or tests including the Stage A rough test, a stage B medium test and a stage I fine test. For the stage A test, a variable N is set equal to 2 as indicated at the top of FIG. 10. (As also indicated, stages B and I differ from stage A and from each other only in the value assigned to the variable N). The purpose of the stage A rough test, as the name implies, is to make a rough determination of an eyeglass prescription for correcting the subject's refractive error.

The first step of the stage A subprogram is to calculate the value of another variable $\Delta D$ which represents a change in the spherical power of the lens system from a so-called current reference prescription (CRP) to be used in the test. At this stage of the process, the CRP corresponds to the objectively determined prescription (block 828, FIG. 8B) initially applied as input data to the computer. The CRP will change in the course of performing the eye examination dependent upon responses elicited from the subject. The value of $\Delta D$, calculated in block 1002, is $1/(N \cdot VA)$, where $N=2$, as previously indicated, and VA represents the visual acuity of the subject determined from the input starting data. After $\Delta D$ is calculated, two trial prescriptions P1 and P2 are calculated as indicated in block 1004, with $P1 = CRP + \Delta D$ and $P2 = CRP - \Delta D$. In the next step, represented by block 1006, the subject is instructed to alternately view two test symbols on the test screen and to indicate a preference between the symbols based on the visual sharpness and clarity of the symbols. The optical system is controlled by the computer to present a power of P1 for the other symbol. (As already described, the optical system power may be automatically changed when the subject changes his direction of gaze from one of two simultaneously presented symbols to the other or the computer may automatically cause the presentation of the test symbol alternately at two locations requiring the subject to involuntarily change his direction of gaze to view the symbol being displayed.) When the subject indicates his preference (either consciously by using the manual response device 122 or unconsciously by way of the VER monitor 596) the computer records the optical system power preferred by the subject as PP. A decision is then made as to whether or not there was a sign reversal as indicated by block 1008. A sign reversal occurs when the subject had previously indicated preferences for steadily increasing or decreasing optical system powers and then indicated a preference for an optical system power which was either a decrease or increase respectively. For example, if the subject had indicated preferences for steadily increasing optical system powers and then expressed a preference for an optical system power which was a decrease from the previous preference, this would constitute a sign reversal. Since, at this stage of the process, the subject has only indicated one preference, there would be no sign reversal so that the program would move to block 1010. If, further along in the process, there is a sign reversal at block 1008, then the computer calculates a new current reference prescription in accordance with the formula of block 1012 of FIG. 10. The term DRP (New) represents the new current reference prescription; the term CRP (Old) represents the old current reference prescription; and the term PP respresents the preferred one of the trial prescriptions P1 or P2 of block 1004.

At block 1010, a decision is made as to whether or not a time out occurred before the subject indicated a preference between the trial prescription P1 and P2. Recall that in one embodiment of the manual response apparatus, timing circuitry was included to provide the computer with a measure of the reaction time of the subject. Thus, if in the subprogram of FIG. 10, the subject fails to express a preference between the trial prescription P1 and P2 within a certain predetermined period of time, visual acuity is tested by the subprogram of FIG. 9 as indicated at block 1014. The subprogram then terminates and the process returns to block 838 of FIG. 8B. If no time out occurs, then the subprogram moves to block 1016 where the new current reference prescription is calculated in accordance with the formula indicated in the block. As indicated in block 1018, the subprogram then makes an objective image quality and refraction measurement to determine whether the accomodative status or image quality has greatly changed, by more than some predetermined amount. If not, the subprogram then returns to block 1004 where two new trial prescriptions P1 and P2 are calculated as previously described. The process is then repeated until at some in the subprogram of FIG. 10, the subprogram concludes and returns to block 838 of FIG. 8B.

Returning to decision block 1018, if the objective refraction has greatly changed, the subprogram tests the visual acuity of the patient, block 1020, using the subprogram according to FIG. 9. After the visual acuity is tested, a decision is made, as indicated by block 1022, whether the visual acuity has fallen. If not, the subprogram returns to block 1004 and continues the process. If the visual acuity has been determined to have fallen, as indicated in block 1024, the patient is given a message via the error routine subprogram set forth in FIG. 13. After the message is given to the patient, the subprogram moves to block 1026, sets the CRP to the prvious CRP giving the best visual acuity and returns to block 1002 to repeat the entire subprogram.

Figure 13:
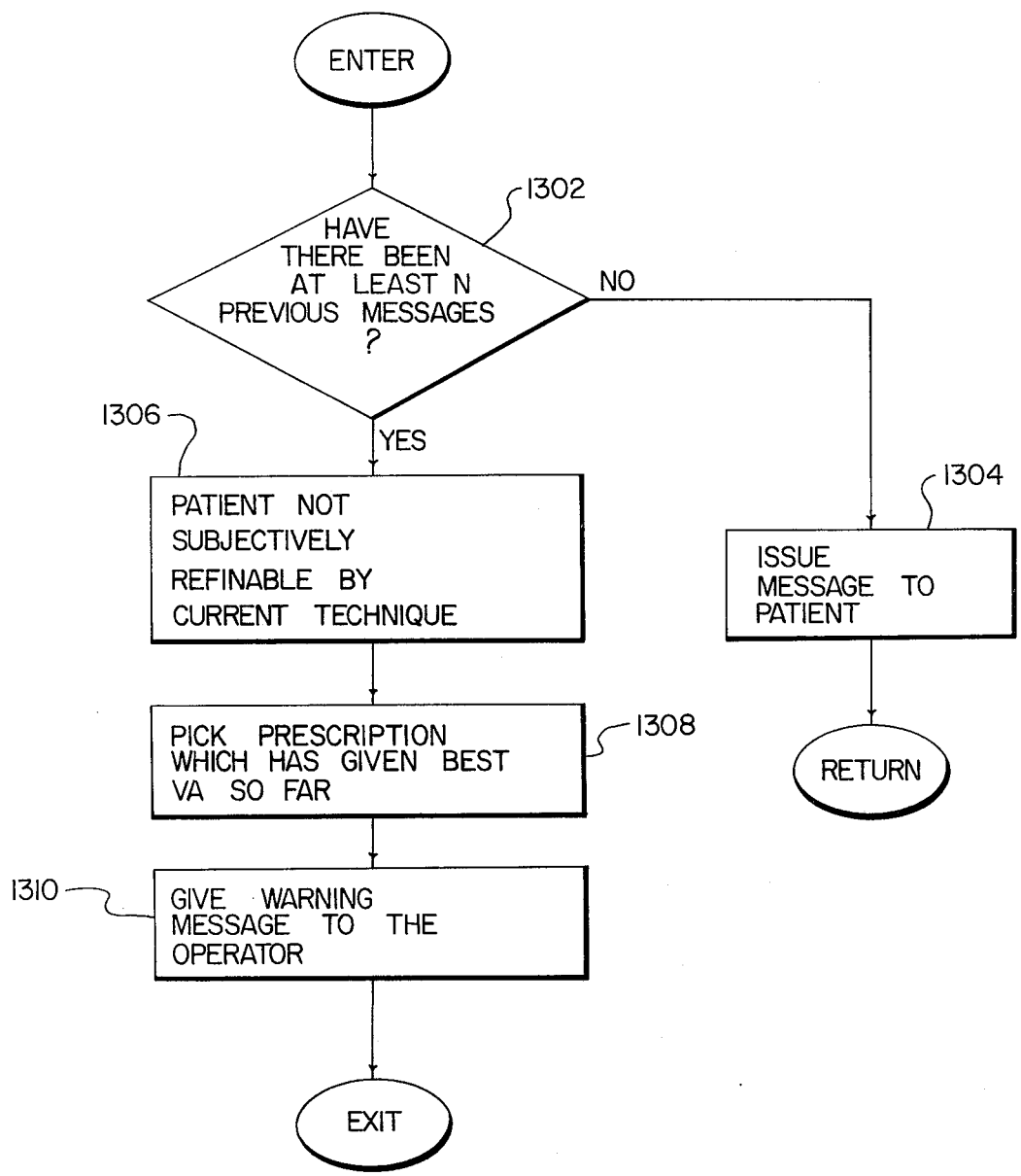

Turning now to the error routine subprogram depicted in FIG. 13, the operator must initially select how many error messages will be given to a patient before the patient is assumed to be not amenable to subjective refraction. The first step in the subprogram in FIG. 13 is indicated at block 1302 as being a determination of whether there have been at least that number of previous messages given to the patient. If not, the subprogram moves to block 1304 and issues a message to a patient. This message is of the type that the patient has made a wrong decision because he has preferred a prescription which resulted in a decrease in his visual accuity rather than an increase. After the patient has been given the message the subprogram returns to block 1026 of FIG. 10. If the patient has been given such a message and predetermined number of times and still chooses a prescription which results in decreased visual acuity, as indicated in block 1306 this means that the patient is not subjectively refinable by the current technique. The subprogram then moves to block 1308 and chooses the prescription which has given the best visual acuity so far. As indicated by block 1310, the operator is then given a message, either by a light flashing, an audible message, a computer printout, or any of of various known techniques, that the patient is not subjectively refractable and has been given the best prescription. The examination is then terminated for that patient.

Regardless of the route taken through the FIG. 9A subprogram, the visual acuity measure of the subject will be made with the current trial lens system setting and a determination made at block 834 of FIG. 8B as to whether the visual acuity is less than 20/80 or not. If the acuity exceeds or equals 20/80, the process moves to block 838. If the acuity is less than 20/80, the stage A test is performed in block 836, as detailed in FIG. 10. When this stage A is completed, the visual acuity is again determined as before the subprogram of FIG. 9 as indicated in block 1014 of FIG. 10. The process then moves to block 838 of FIG. 8B. If at block 838 of at 1014 of FIG. 10, the visual acuity is determined to be better than 20/40, the process moves to block 858 of FIG. 8B. If, at block 838, the visual acuity is less than 20/40, the process moves to block 840 where a stage B medium test is performed.

This test is the same as the previously described stage A test of FIG. 10 except that the variable N is set equal to 4 rather than 2. The significance of the value 4, as opposed to the value 2, for the variable N is that the change in optical system power presented to the subject is in a smaller increment. That is, the greater is the value of the variable N. the smaller is the incremental change in the optical system power.

After the stage B test is performed and the visual acutiy is determined, a determination is made as to whether this visual acuity is better than 20/100 and if it is, the process moves to block 846. If it is not, the process moves to block 844 where a stage C rough test is performed. This test is illustrated by a flow chart in composite FIG. 11 which also represents stage D, G and J tests to be described later.

The process for performing the stage C, D, G and J tests is the same except that the values assigned to four variables N1, N2, N3, A and B are different for each test. For the stage C test, the values of the variables are indicated in the first column under the letter C in the table shown at the top of FIG. 11A. Specifically, variable N1 has a value of 4, variable N2 has a value of 2, variable N3 has a vlaue of 2, variable A has a value of 90°, and variable B has a value of 0.25. The angle designated by the variable A represents an angular distance of the optical system trial cylinder (i.e., the variable crossed cylinder 116) measured in a standard cartesian coordinate system fixed in the subject's frontal plane.

The function of the stage C rough test is to make a rough determination of the subject's astigmatic axis (if any exists). In the first step of the test, represented by block 1102, a determination is made as to whether the current reference prescription contains a cylinder component, i.e., any cylindrical power along with the spherical power. At this stage of the test, no cylinder component would be present in the current reference prescription unless the subject's initial objective refraction prescription as determined in block 828 of FIG. 8B had contained such a component. If no component is present, the process moves to block 1106 where two new trial prescriptions are calculated, one having a cylinder component whose axis is oriented at $A=90°$ (vertical and the other having a cylinder component whose axis is oriented at $A+90° = 180°$ (horizontal). The cylindrical power of each new trial prescription in $1/N_2VA$, as indicated in block 1106, and the spherical power is $CRP-1/N_1VA$, a value sufficient to compensate for the added cylindrical power so that the result spherocylindrical power of the two trial prescriptions is the same as the current reference prescription.

The two new trial prescriptions are then presented to the subject in the manner already discussed and if one is preferred it is recorded as P.P. (block 1108). If in block 1102 it had been determined that the current reference prescription contained a cylinder component, then two new test axes for the cylinder component are calculated as indicated in block 1104, where CA represents current axis and D represents the power of the cylinder component. These two test axes would be presented to the subject to ascertain his preference (block 1108) and any preference would be recorded as P.P. After the two alternatives are presented to the subject (whether they be the two new trial prescriptions or the new test axes for the cylinder component), a determination is made as to whether a preference was expressed before a "time out" (block 1110). If not, the process returns to block 846 of FIG. 8C. If so, the process moves to block 1112 of FIG. 11B.

Figure 11A:
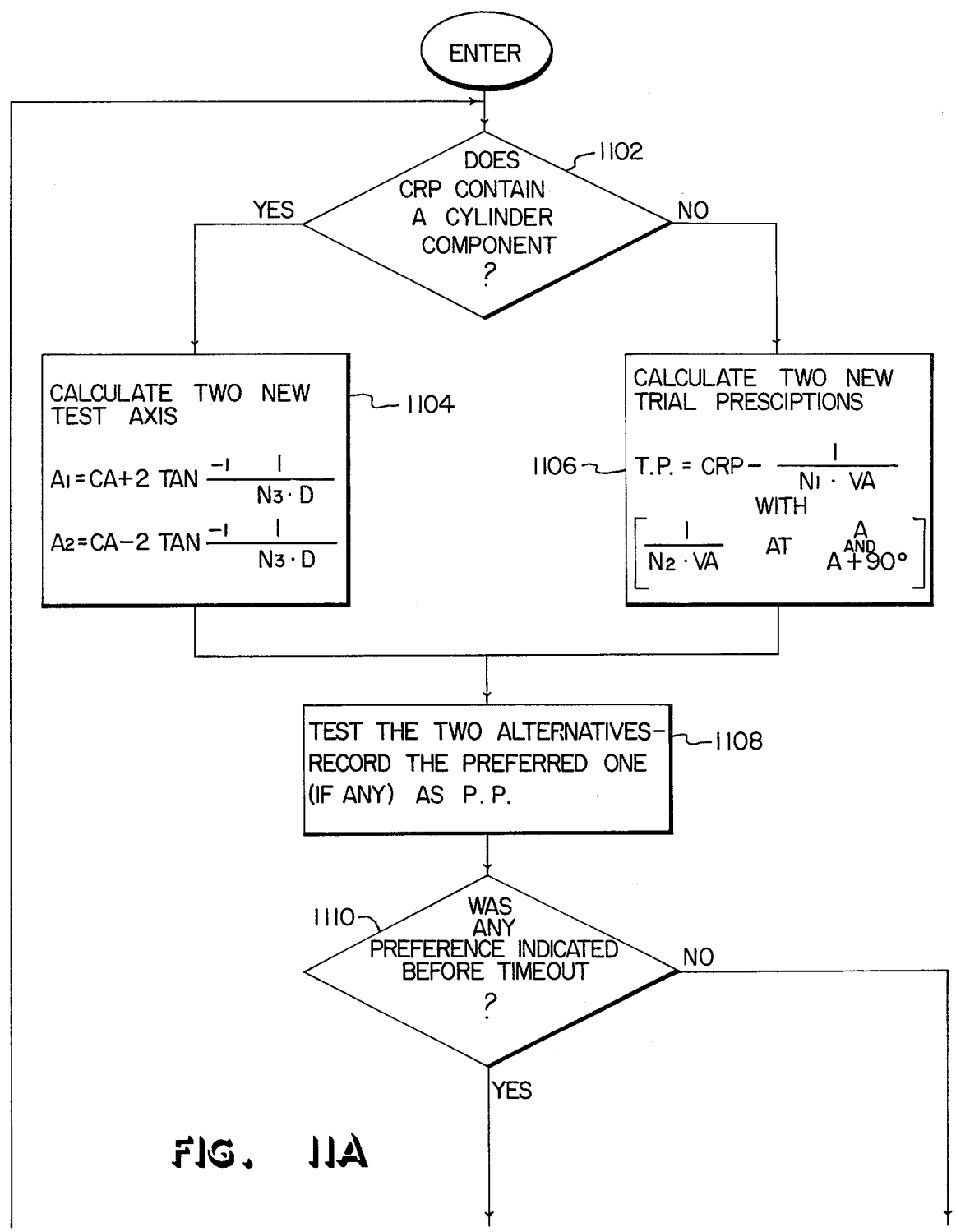
Figure 11B:
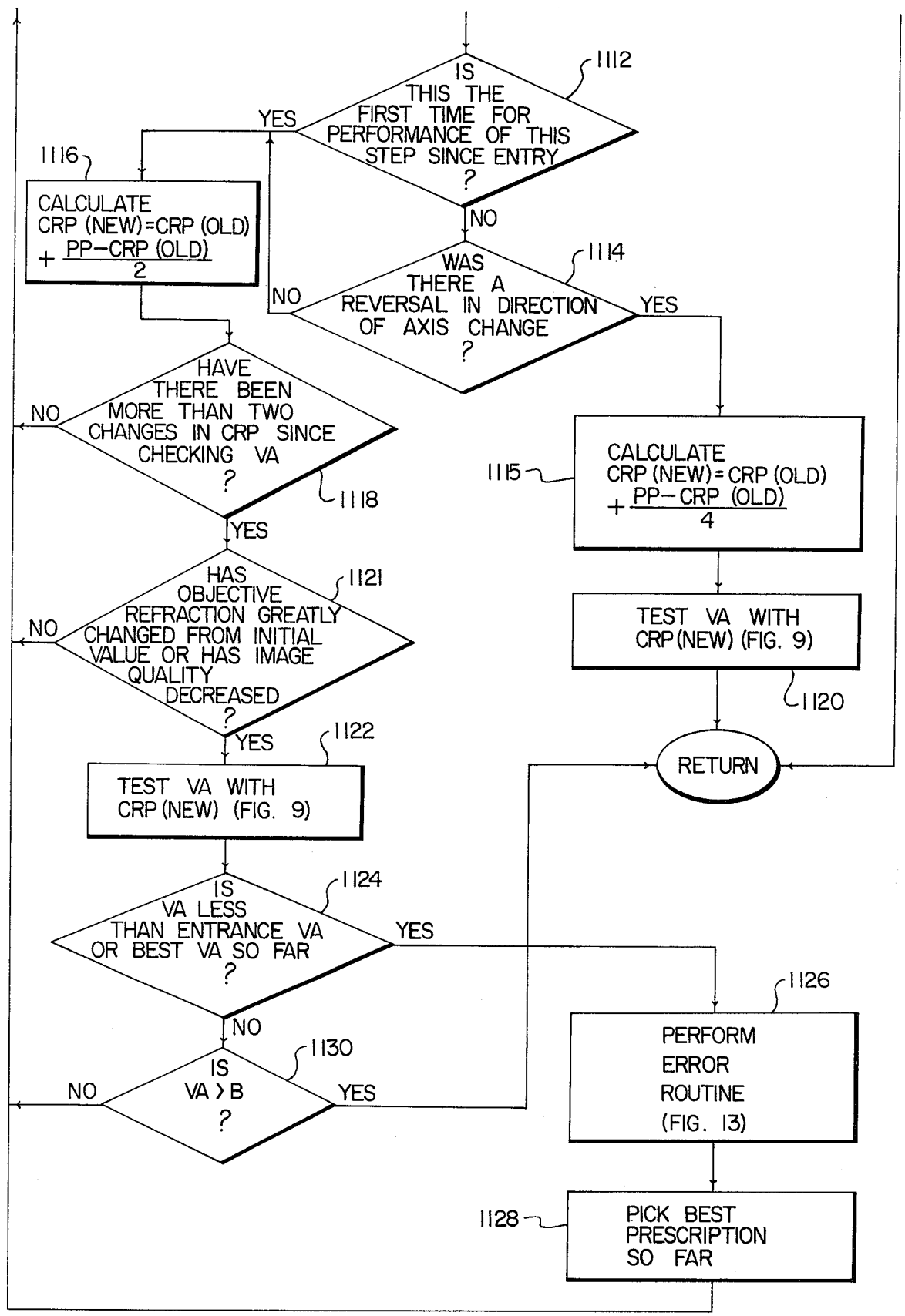
Figure 12A:
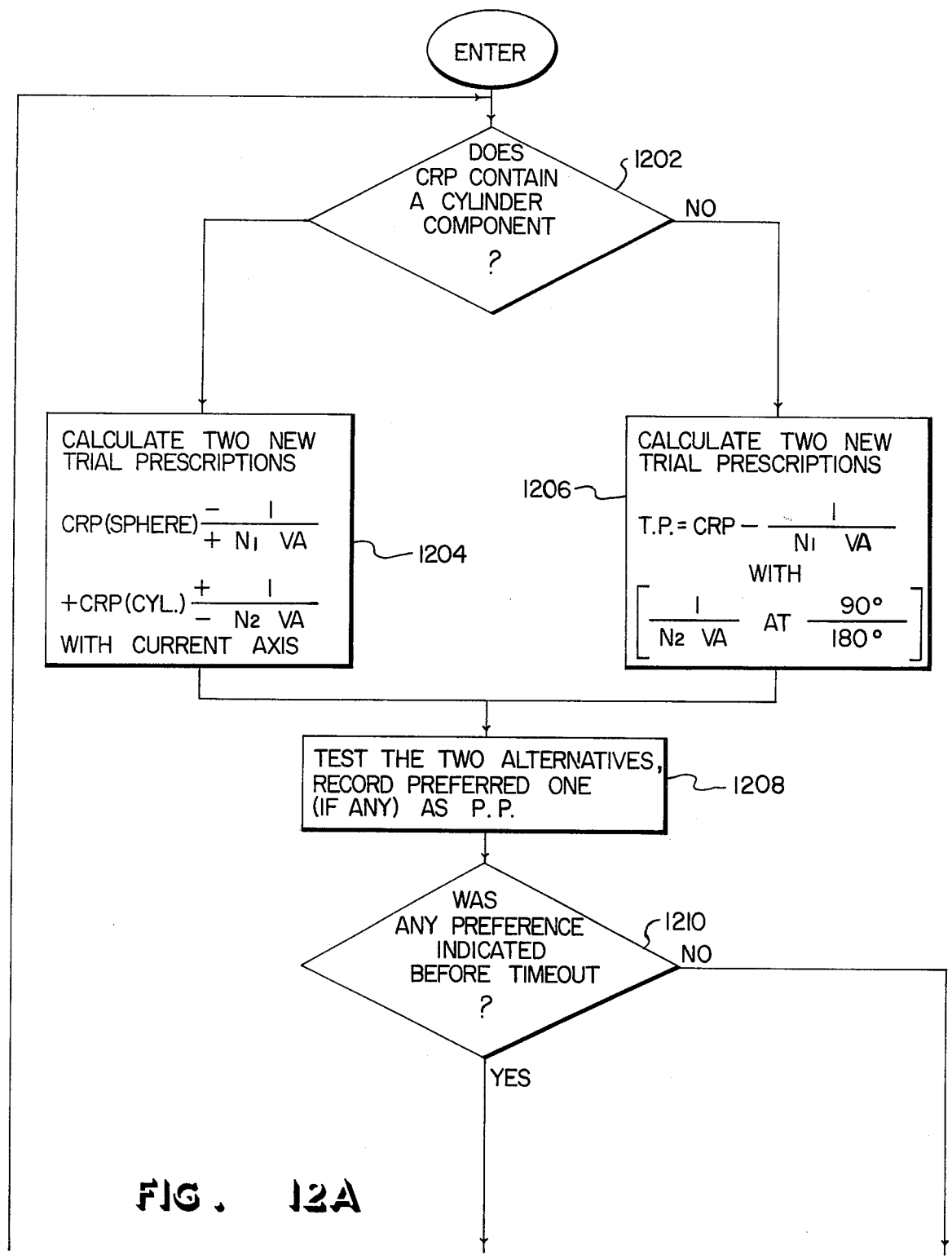
Figure 12B:
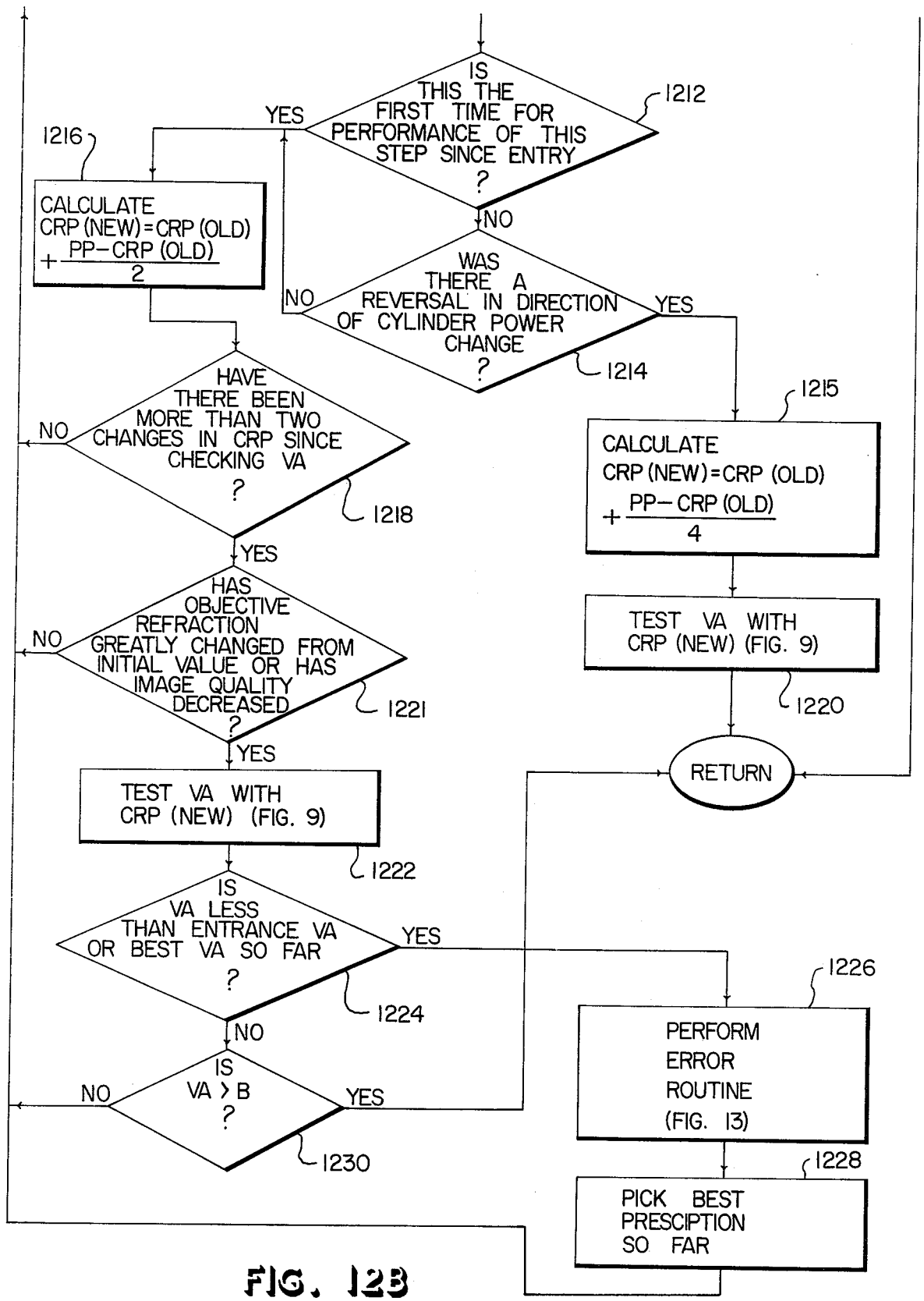

The function of the step represented by block 1112 is to determine if the subprogram a composite FIG. 11 had previously gotten as far as block 1112 since the calling of the subprogram, i.e., whether this performance of the step of block 1112 is the first since entry in the subprogram. If the step had been performed previously, the process moves to block 1114 where a determination is made as to whether there was a reversal in the direction of cylinder axis change with the last preference expressed by the subject. The meaning of this can best be understood by way of example. Assume that for successively presented pairs of cylinder axis positions, the subject each time indicates a preference for the axis positions which is at an angle greater than that of the immediately preceding preference, and than that the subject finally indicates a preference for an axis position which is at an angle less than that of the previous preference. This contitutes a "reversal in the direction of cylinder axis change." If it is determined in block 1114 that such a reversal has occurred, the process moves to block 1115 where a "new" current reference prescription is calculated in accordance with the formula shown in the block. With the optical system set at this prescription, the subject's visual acuity is tested, as indicated in block 1120, as described earlier in connection with FIGS. 9A and 9B. The subprogram of FIGS. 11A and 11B then returns to block 846 of FIG. 8C.

If it had been determined in either block 1112 that the step represented by the block had not been previously performed since entry or in block 1114 that no reversal had occurred, then the process would have moved to block 1116 for calculation of a "new" current reference prescription. The only difference between the current reference prescription calculated in block 1116 and that calculated in block 1115 is that the latter constitutes a smaller change from the "old" CRP than does the former. The significance of this is that in the latter case, the examination is getting closer to determining the prescription necessary to correct the subject's astigmatic error and these smaller changes are warranted so as not to "overshoot" the ultimate prescription desired. After the new CRP is calculated in block 1116, the program moves to block 1118 and then, if there had been more than two changes in the CRP since testing the subject's visual acuity, on the block 1121, otherwise it returns to block 1102. In block 1121, a determination is made whether the objective refraction or image quality has greatly changed from its initially determined value. If so, on to block 1122, otherwise the subprogram returns to block 1102. In block 1122, the subject's visual acuity is tested with the new CRP. In block 1124, a determination is made whether the visual acuity is less than the initial visual acuity or the best so far. If so, a message is given the patient per the FIG. 13 subprogram, as indicated by block 1126, and the best prescription so far is picked, as indicated by block 1128. If the visual acuity had not fallen, the subprogram moves to block 1130. The next step (block 1130) is to determine if the subject's visual acuity is better than the variable B, which for the stage C test is set equal to 0.25. If it is, the program returns to block 846 of FIG. 8C, otherwise the program returns to block 1102.

Returning now to the general program of FIG. 8C, and in particular to block 846 which represents the next step following the performance of the stage C rough test, there it is indicated that a determination is made as to whether the subject's visual acuity (with the CRP) is better than 20/40. If it is, the program moves to block 858, and if it is not, the program moves to block 848 where a stage D rough test is performed. Except for the value at which the variables N1, N2, N3 A and B are set, the stage D rough test is the same as the stage C test just described.

At this point, a comment might be made regarding the selection of the Axis of the cylinder component. Although not shown in the flow charts, provision might be made for making a determination as to whether the axis of the cylinder component has, through preferences expressed by the subject, been moved through 180°. If it has, then the cylinder axis may be fixed simply at that position where the subject's visual acuity is maximum of the cylinder may be eliminated altogether should the visual acuity not change with changes in the cylinder axis. With the illustrative method disclosed, in which choices are based on visual acuity, the above-mentioned provision may be unnecessary.

After performing the stage D test, a determination is again made as to whether the subject's visual acuity is greater than 20/40 as indicated in block 850. If it is, the program moves to block 858, and if it is not, the program moves to block 852 where a so-called stage E rough test subprogram is called. This subprogram is illustrated by the flow chart in composite FIG. 12. The FIG. 12 flow chart also represents so-called stages H and K tests with the only difference between these tests and the stage E test being the value of variables N1, N2, and B as shown in the table at the top of FIG. 12A. The function of the FIG. 12 subprogram is to assist in determining the power of the subject's astigmatic error, if any. A comparison of the composite FIT. 11 subprogram with the composite FIG. 12 subprogram reveals that the two subprograms contain the same number of steps, most of which are identical. The principal difference is between block 1204 of FIG. 12A and the corresponding block 1104 of FIG. 11A in which in the former, two new trial prescriptions are calculated to provide the cylinder component with new alternative power settings whereas in the latter, two new test axes are calculated. In view of the similarities between the two subprograms, no detailed discussion will be given of the FIG. 12A and 12B subprogram.

After performing the stage E rough test of composite FIG. 12, the process of composite of FIG. 8 proceeds to block 854 where a determination is again made as to whether the subject's visual acuity is greater than 20/40. If it is, the process moves to block 858 and if it is not, the process moves to block 856 where a stage B medium test is performed. This test is illustrated by flow chart in FIG. 10 which was discussed earlier in conjunction with the stage A test. In the stage B test, the variable N is set equal to 4 rather than 2 as in the stage A test.

If, in any of the steps represented by block 848 of FIG. 8B, 846, 850 or 854 of FIG. 8C, it is determined that the subject's visual acuity is better than 20/40, or after performing the stage B medium test of block 856, the process moves to block 858 of FIG. 8C. There, a determination is made as to whether the subject's visual acuity is better than 20/20. If it is, the process moves to block 866 of FIG. 8D, otherwise the process moves to block 860 of FIG. 8D. In block 860, a stage G medium test is performed in accordance with the flow chart of composite FIG. 11 already described. After the stage G medium test, the process again makes the determination at block 862 as to whether the subject's visual acuity is better than 20/20. If it is determined that it is not, the process moves to block 864 where a stage H medium test is performed in accordance with the flow chart of FIG. 12. If visual acuity at block 862 exceeds 20/20, the process moves to block 866. Next, in order, a stage I fine test is performed in accordance with the subprogram of FIG. 10, a stage J fine test is performed in accordance with the subprogram of composite FIG. 11, and a stage K fine test is performed in accordance with the subprogram of composite FIG. 12 (block 866). A determination is then made at block 868 as to whether the subject's current reference prescription has changed since the most recent entry of block 866 and if it has, the tests shown in block 866 are again performed, otherwise the process causes the computer system to see whether the balancing option was selected (block 870). If not, the system generates an output data (block 872) obtained from performing the eye examination. This output data would consist of a lens prescription together with a vertex distance for correcting the subject's refractive error and, if desired, the subject's visual acuity with the trial lens system set at the final prescription. This information, of course, would be provided for both eyes of the subject.

Returning to block 870, the operator must input into the system whether or not a balancing routine is desired. There are several instances where balancing the prescription of both eyes would not be performed, for example, if paralytic (cycloplegic) drops are utilized or if the patient cannot be balanced bacause the eyes are so incomparable, such as if one eye had a cataract. If the balancing option was selected, the subprogram moves to block 874 and performs the balancing routine in accordance with the subprogram set forth in FIG. 14, after which the subprogram moves to block 872 and generates the output data.

Figure 14:
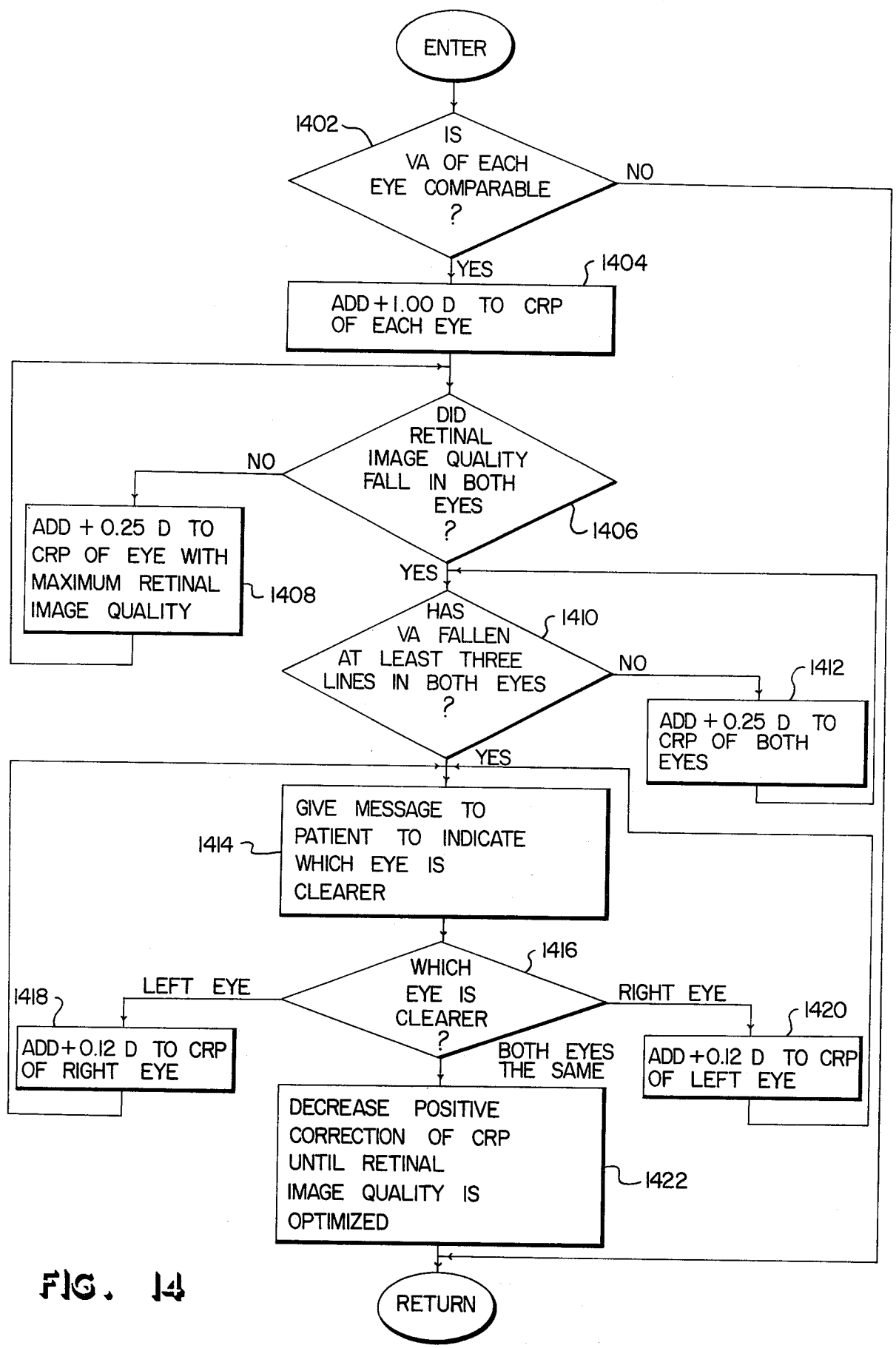

Referring now to FIG. 14 wherein there is depicted a flow chart of a balancing routine, the first step is at a block 1402 wherein a determination is made as to whether the visual acuity of each eye is comparable. If not, the subprogram does not perform any balancing and returns to block 872 of FIG. 8D. If the visual acuity of the eyes are comparable, the subprogram moves to block 1404 and adds 1.00 diopter to the current reference prescription of each eye. The system then checks the retinal image quality in both eyes and determines whether or not it fell in both eyes, as indicated in block 1406. If the retinal image quality did not fall in both eyes, the subprogram moves to block 1408, adds 0.25 diopter to the CRP of the eye with the maximum retinal image quality and returns to decision block 1406. This continues until the retinal image quality falls in both eyes, at which point the subprogram moves to block 1410. An alternative means of accomplishing this is by checking the objective refraction with each addition of plus lens to see if the patient was able to relax accomodation. In block 1410 the system determines whether the visual acuity has fallen at least three lines (on the standard Snellen chart) in both eyes. If not, the subprogram moves to block 1412 and adds 0.50 diopter to the CRP of both eyes and returns to block 1410. This process continues until the visual acuity falls at least three lines in both eyes. After that has occurred, the subprogram moves to block 1414. The patient is given a message to indicate via the manual response unit which eye is clearer. The machine, of course will display the target to only one eye at a time. The system then interprets the patient's response, as indicated in block 1416. If the patient indicates that the left eye is clearer, the subprogram moves to block 1418 and adds 0.12 diopter to the CRP of the patient's right eye and returns to block 1414. If the patient indicated that the right eye was clearer, the subprogram moves to block to block 1420 and adds 0.12 diopter to the CRP of the left eye and then moves to block 1414. After the patient finally responds that both eyes are the same, the subprogram moves to block 1422, at which point the system decreases the positive correction of the current reference prescription until the retinal image quality is optimized. The subprogram then returns to block 872 of FIG. 8D.

In the manner shown and described, apparatus and method are provided for performing refractive error measurement under control of a programmed automatic data processing system. As illustrated in the program represented by the flow chart of composite FIG. 8 and the subprograms represented by the flow charts of FIGS. 9 through 12, both objective and subjective eye tests are performed under control of the data processing system in determining the subject's refractive error. The power of the optical system of the apparatus may be varied in a continuous manner, also under control of the data processing system, to provide a wide range of lens powers which may be presented to the subject while maintaining constant the number of lenses which are placed before the subject. Visual stimuli are automatically presented to the subject for viewing through the optical system and the subject is instructed as to use of a manual response device for responding to the stimuli. Some of the stimuli consist of pairs of symbols successively presented on a screen for which the subject is to indicate a preference for one symbol of each pair. Even though the power of the optical system may be different for viewing one symbol of the pair from that for viewing the other symbol, the apparent symbol size is automatically maintained constant to thereby eliminate what might otherwise be a preference bias by the subject for larger size symbols. The subject's responses to the test stimuli presented are utilized by the data processing system in determining subsequent test stimuli to present to the subject.

Throughout the entire examination procedure, objective measurements are made on the subject's refractive power and material images quality as a means of monitoring the subjective responses of the patient. If the patient subjectively responds in a manner which contradicts the objective refraction measurement, the patient is given a message and the test repeated. In this manner, checks and balances are provided so that the likelihood of getting the best prescription for the patient is maximized. Additionally, if the patient cannot be subjectively refined, the disclosed method and apparatus provides an objective prescription.

Although the invention has been described with reference to particular preferred embodiments thereof, many changes and modifications will become apparent to those skilled in the art in view of the foregoing description which is intended to be illustrative and not limiting of the invention defined in the appended claims.

What is claimed is:

1. Apparatus for measuring refractive error of a subject's eye comprising:
   a subjective refraction system including:
   a first optical system including display means for displaying test symbols, said first optical system being continuously variable over a range of powers through which the subject views the displayed test symbols;
   first control means for setting said first optical system at any selected power setting within said range of powers; and
   a manual response device operable by the subject for providing a plurality of output signals;
   an objective refraction system including;
   pattern generating means for generating an optical pattern;

a second optical system continuously variable over said range of powers through which said optical pattern is imaged on the retina of the subject's eye;

second control means for setting said second system at any selected power setting within said range of powers;

refraction measurement means adapted to view the retinal image of the pattern through said second optical system and provide an output signal indicative of the total refraction of the eye and the second optical system; and image quality measurement means adapted to view the retinal image of the pattern through said second optical system and to respond to contrast transmission effects in the image to provide an output signal indicative of the image quality; and data processing system means coupled to said first and second control means, said display means, said manual response device, said refraction measurement means and said image quality measurement means and responsive to signals received from said response device, said refraction measurement means and said image quality measurement means to control said first and second control means to identically set the first and second optical systems at discrete settings of cylinder and spherical power which provide a refractive correction most desired by the subject which is consistent with refraction and image quality measurements.

2. The apparatus of claim 1 wherein said first and second optical systems share a common variable crossed cylinder.

3. The apparatus of claim 1 wherein said display means includes:
a planar screen movable along a line perpendicular to its plane;
means for projecting light images of the test symbols onto the screen; and
focus means coupled to said projecting means for maintaining the projected images on the screen in focus.

4. The apparatus of claim 3 wherein said first control means include means for moving said screen and controlling said focus means to effect a power setting for said first optical system.

5. The apparatus of claim 1 wherein said display means further includes means for displaying moving bars to the subject and said subjective refraction system further includes means for monitoring, under control of the data processing system means, the direction of gaze of the subject for determining if the subject's eyes exhibit a reflex following movement with the moving bars.

6. The apparatus of claim 1 wherein said pattern generating means includes means for generating a moving pattern of alternating dark and light bars and said refraction measurement means includes a retinoscopy analysis circuit.

7. The apparatus of claim 1 wherein said pattern generating means includes means for generating a moving pattern of alternating dark and light bars and said image quality measurement means includes:
photoconductive means for providing an output signal as a function of the amount of light impinging thereon, said photoconductive means being positioned with respect to said second optical system so that the retinal image of the moving pattern is focused on said photoconductive means;
differentiating means coupled to receive the output signal from said photoconductive means for providing a signal which is indicative of the rate of change of the photoconductive means output signal; and
image quality analysis means coupled to receive said differentiating means signal for providing to said data processing system means a signal which is a measure of the value of said differentiating means signal.

8. The apparatus of claim 1 wherein said second optical system includes a spherical lens movable along its axis and said second control means includes means for positioning said spherical lens to effect a power setting for said second optical system.

9. The apparatus of claim 1 wherein said display means includes means for projecting light images of the test symbols and said first control means includes focus means for controlling the plane of focus of said light images to effect a power setting for said first optical system.

10. The apparatus of claim 9 wherein said projecting means further includes means for projecting light images of moving bars and said subjective refraction system further includes means for monitoring, under control of the data processing system means, the direction of gaze of the subject for determining if the subject's eyes exhibit a reflex following movement with the moving bars.

11. The apparatus of claim 10 wherein said projecting means comprises:
means for projecting a beam of light;
first holding means for holding a plurality of transparencies, each of said transparencies containing a different test symbol image with one of said transparencies being clear;
first positioning means operating under the control of said data processing system means for selectively positioning said holding means so that a desired one of said transparencies is in the path of said light beam;
second holding means holding a clear transparency and a plurality of transparency bars;
second positioning means operating under the control of said data processing system means for alternatively positioning said clear transparency in the path of said light beam or moving said transparency bars through the path of said light beam; and
means for controlling said first and second positioning means so that when a test symbol is to be projected the clear transparency of said second holding means is positioned in the path of said light beam and when moving bars are to be projected the clear transparency of said first holding means is positioned in the path of said light beam.

12. In an automatic process for subjectively determining the refractive error of a subject wherein the power of an optical system presented to the subject is controlled by a data processing system is response to responses derived from the subject choosing between choices of images presented to the subject until an optimum power is determined and thereafter providing a readout of a lens prescription which provides refractive correction for the subject, wherein the process comprises repeating at frequent intervals the steps of:

(a) determining under control of the data processing system the visual acuity of the subject when viewing test stimuli through an optical system set at a selected power;

(b) presenting test stimuli for viewing by the subject through the optical system set alternatively at the selected power $+\Delta D$ and at the selected power $-\Delta D$, where $\Delta D$ has a first value if the visual acuity is determined in step (a) to be greater than a predetermined threshold value and where $\Delta D$ has a second value greater than said first value, if the visual acuity is determined in step (a) to be less than the threshold value; and (c) determining under control of the data processing system whether one of the power settings of selected power $+\Delta D$ or $-\Delta D$ is preferred by the subject over the other for viewing the test stimuli;

the improvement comprising the steps of:

(d) objectively refracting the subject with the preferred power setting of the system after step (c);

(e) measuring retinal image quality of the subject, including cotrast transmission effects, with the preferred power setting of the system;

(f) determining, under control of the data processing system, whether the objective refraction or retinal image quality has changed more than a threshold amount;

(g) if the objective refraction or retinal image quality has not changed more than the threshold amount, returning to step (a);

(h) if the objective refraction or retinal image quality has changed more than the threshold amount, determining the visual acuity of the subject;

(i) determining if the visual acuity of the subject has fallen;

(j) if the visual acuity has not fallen, returning to step (b);

(k) if the visual acuity has fallen, determining whether the subject has been given an error message more than a predetermined number of times;

(l) if the subject has not been given the error message more than a predetermined number of times, give the error message to subject that his preferred power is inconsistent with objective measurements and return to step (c); and (m) if the subject has been given the error message more than the predetermined number of time, choosing prescription which has given best visual acuity so far.

* * * * *